US010101276B2

(12) United States Patent
Kimura et al.

(10) Patent No.: US 10,101,276 B2
(45) Date of Patent: Oct. 16, 2018

(54) SCREENING APPARATUS AND SCREENING METHOD

(71) Applicant: Furukawa Electric Co., Ltd., Tokyo (JP)

(72) Inventors: Kenichi Kimura, Tokyo (JP); Ken Tsukii, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 14/667,465

(22) Filed: Mar. 24, 2015

(65) Prior Publication Data
US 2015/0198537 A1 Jul. 16, 2015

Related U.S. Application Data

(63) Continuation of application No. PCT/JP2013/066442, filed on Jun. 14, 2013.

(30) Foreign Application Priority Data

Oct. 9, 2012 (JP) .................................. 2012-224512

(51) Int. Cl.
*G01N 21/76* (2006.01)
*G01N 21/13* (2006.01)
(Continued)

(52) U.S. Cl.
CPC ............. *G01N 21/76* (2013.01); *B01L 3/021* (2013.01); *G01N 15/1463* (2013.01);
(Continued)

(58) Field of Classification Search
None
See application file for complete search history.

(56) References Cited

U.S. PATENT DOCUMENTS 5,377,636 A * 1/1995 Rix ......................... F02M 59/30
123/446
6,497,155 B1 * 12/2002 Feygin .................. G01N 35/10
422/63
(Continued)

FOREIGN PATENT DOCUMENTS

JP 11-326152 11/1999
JP 11326152 A * 11/1999
(Continued)

OTHER PUBLICATIONS

International Search Report dated Aug. 13, 2013 in PCT/JP2013/066442 filed Jun. 14, 2013 (with English Translation).
(Continued)

*Primary Examiner* — Benjamin R Whatley
(74) *Attorney, Agent, or Firm* — Oblon, McClelland, Maier & Neustadt, L.L.P.

(57) ABSTRACT

A screening apparatus includes a light permeable measurement chip having a well retaining a liquid including microparticles, a measuring section acquiring optical information of the microparticles obtained by illuminating the microparticles, an analyzing section that extracts optical information of the microparticles, a receiving plate receiving a microparticle selectively picked up from the measurement chip, a moving section moving the measurement chip and the receiving plate against the measuring section, and a collecting section for collecting a microparticle by sucking with the suction-ejection capillary and ejecting on the receiving plate. A distal-end outer dimension of the capillary is greater than a width of the well. The capillary sucks the target microparticle at a position where the distal end of the capillary and the measurement chip are spaced by a predetermined distance and a central axis of the distal end of the
(Continued)

capillary and a central axis of the well are mutually displaced.

17 Claims, 26 Drawing Sheets

(51) Int. Cl.
*B01L 3/02* (2006.01)
*G01N 21/03* (2006.01)
*G01N 21/11* (2006.01)
*G01N 15/14* (2006.01)
G01N 35/02 (2006.01)
G01N 21/64 (2006.01)
G01N 15/10 (2006.01)

(52) U.S. Cl.
CPC ............. *G01N 21/03* (2013.01); *G01N 21/11* (2013.01); *G01N 21/13* (2013.01); *B01L 2200/0642* (2013.01); *B01L 2200/0647* (2013.01); *B01L 2200/0652* (2013.01); *B01L 2300/0627* (2013.01); *B01L 2300/0838* (2013.01); *B01L 2300/165* (2013.01); *G01N 21/6452* (2013.01); *G01N 35/028* (2013.01); *G01N 2015/1006* (2013.01); *G01N 2015/149* (2013.01); *G01N 2015/1477* (2013.01); *G01N 2021/0346* (2013.01); *G01N 2021/135* (2013.01); *G01N 2201/12* (2013.01); *G01N 2500/10* (2013.01)

(56) References Cited

U.S. PATENT DOCUMENTS

| | | | |
|---|---|---|---|
| 6,887,431 | B1 | 5/2005 | Vann et al. |
| 2003/0021734 | A1 | 1/2003 | Vann et al. |
| 2004/0086426 | A1 | 5/2004 | Vann et al. |
| 2004/0136870 | A1* | 7/2004 | Kochy ............... G01N 15/1456 422/73 |
| 2005/0130318 | A1 | 6/2005 | Vann et al. |
| 2005/0271550 | A1* | 12/2005 | Talmer .................. B01L 3/5082 422/400 |
| 2006/0012130 | A1 | 1/2006 | Vann et al. |
| 2007/0238162 | A1* | 10/2007 | Miyamoto ........... G01N 21/253 435/287.2 |
| 2012/0045366 | A1* | 2/2012 | Katsumi ............ G01N 35/1011 422/67 |
| 2013/0017129 | A1* | 1/2013 | Shioyama .............. C12M 45/02 422/513 |
| 2013/0037059 | A1* | 2/2013 | Stafford ................ B01L 3/5085 134/21 |

FOREIGN PATENT DOCUMENTS

| | | | |
|---|---|---|---|
| JP | 2003-517581 | A | 5/2003 |
| JP | 2005-172707 | A | 6/2005 |
| JP | 2007-326072 | A | 12/2007 |
| JP | 2008-249679 | A | 10/2008 |
| JP | 2009-270875 | A | 11/2009 |
| JP | 2010085343 | A * | 4/2010 |

OTHER PUBLICATIONS

Written Opinion dated Aug. 13, 2013 in PCT/JP2013/066442 filed Jun. 14, 2013.
Office Action dated Feb. 24, 2014 in Japanese Patent Application 2013-553179 (with English Translation).
Office Action dated Jun. 16, 2014 in Japanese Patent Application No. 2013-553179 (with English Translation).
Decision to Grant a Patent dated Sep. 16, 2014 in Japanese Patent Application No. 2013-553179 (with English Translation).
Supplementary Search Report dated Apr. 25, 2016 in European Patent Application No. 13845401.2.
Notification Concerning Transmittal of International Preliminary Report on Patentability dated Apr. 23, 2015 in PCT/JP2013/066442.
International Preliminary Report on Patentability and Written Opinion dated Apr. 14, 2015 in PCT/JP2013/066442 (submitting English translation only).
Combined Chinese Office Action and Search Report dated Dec. 14, 2015 in Patent Application No. 201380045162.0 (with English Translation).
Chinese Office Action dated Jul. 20, 2016 in Patent Application No. 201380045162.0 (with English translation).
Chinese Office Action dated Nov. 28, 2016 in Patent Application No. 201380045162.0 (with English translation).
Extended European Search Report dated Sep. 29, 2016 in Patent Application No. 13845401.2.
Office Action cited in Chinese Application No. 201380045162.0 dated May 17, 2017.

* cited by examiner

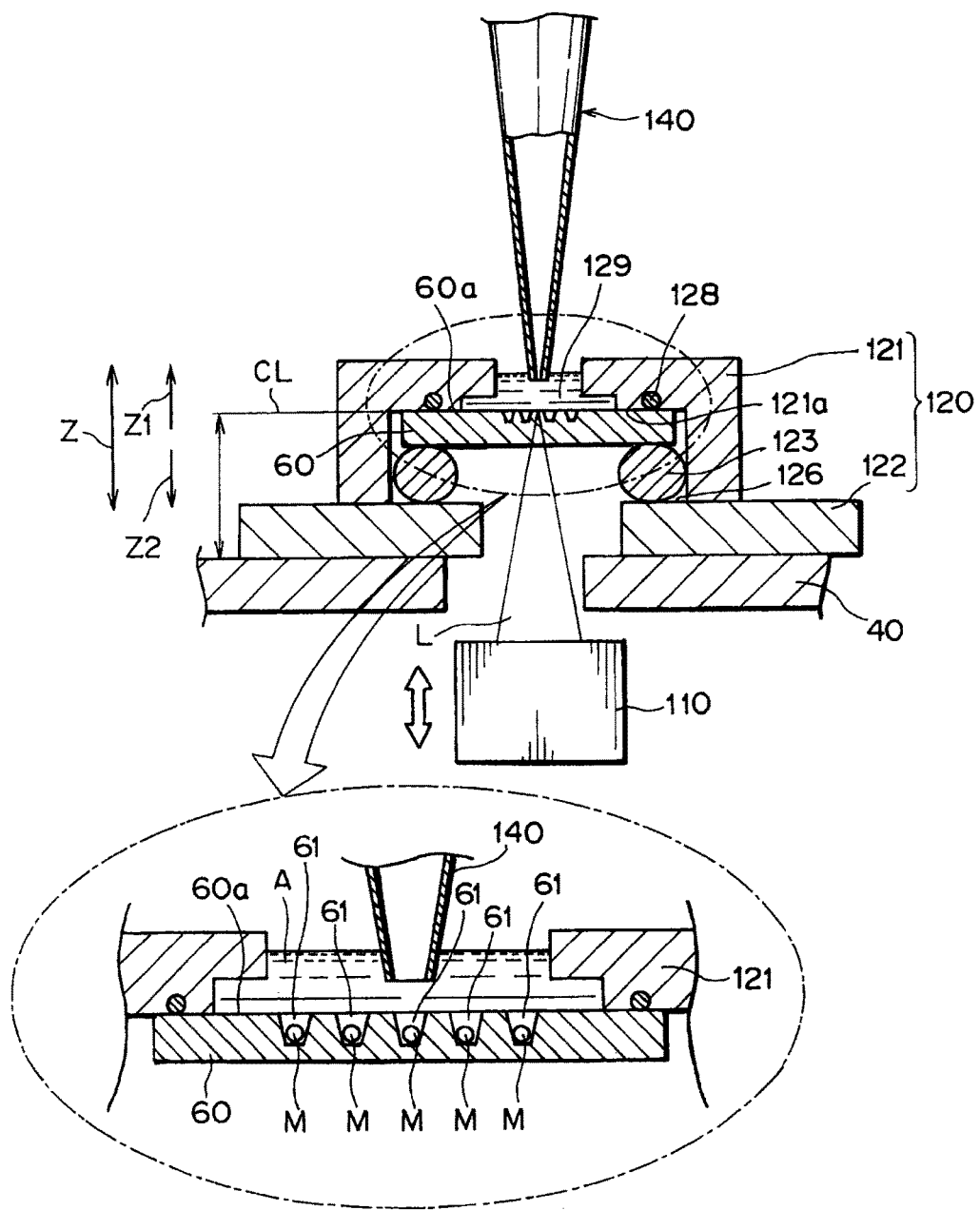
F I G. 5

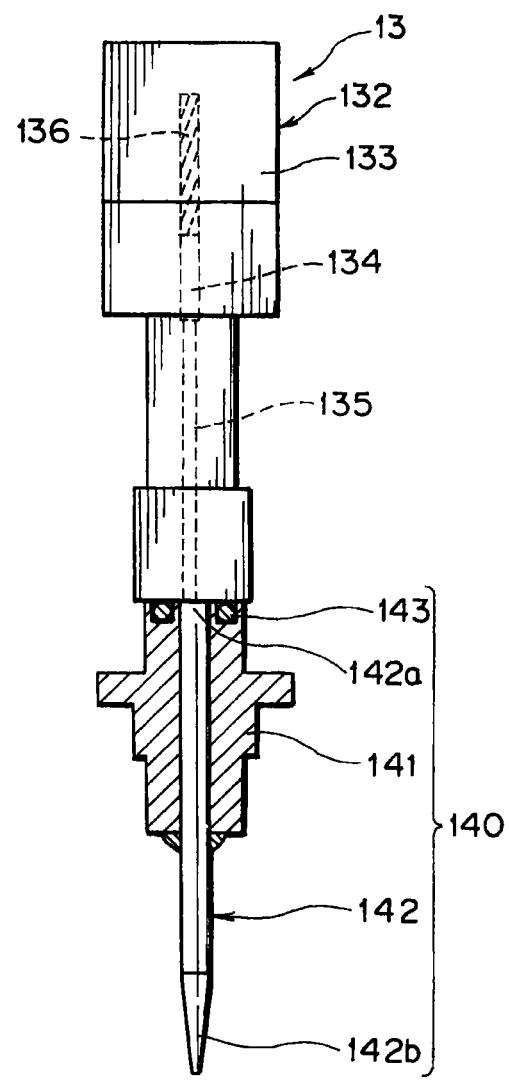
F I G. 7

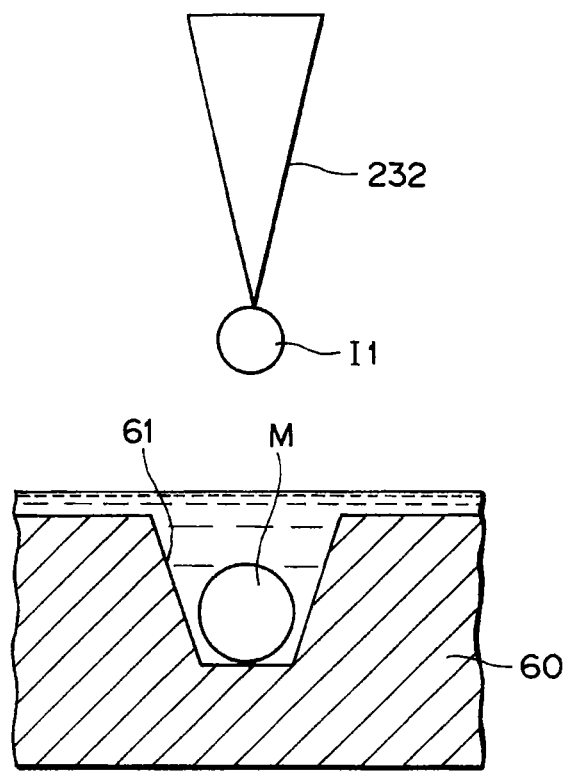
F I G. 1 3 A
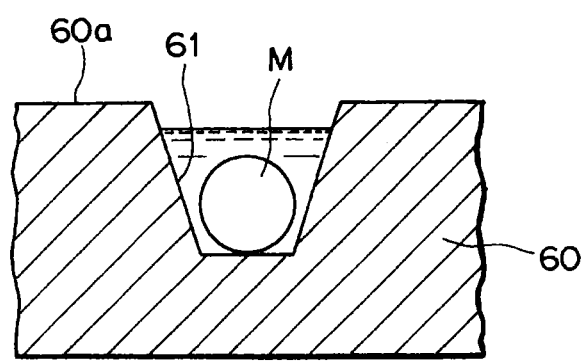
F I G. 1 3 B

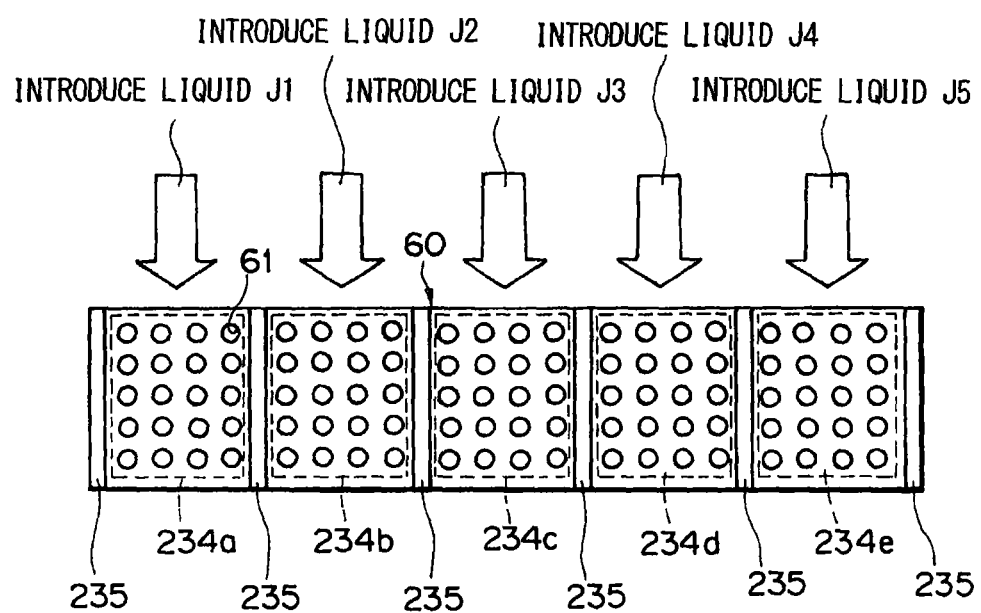
F I G. 14

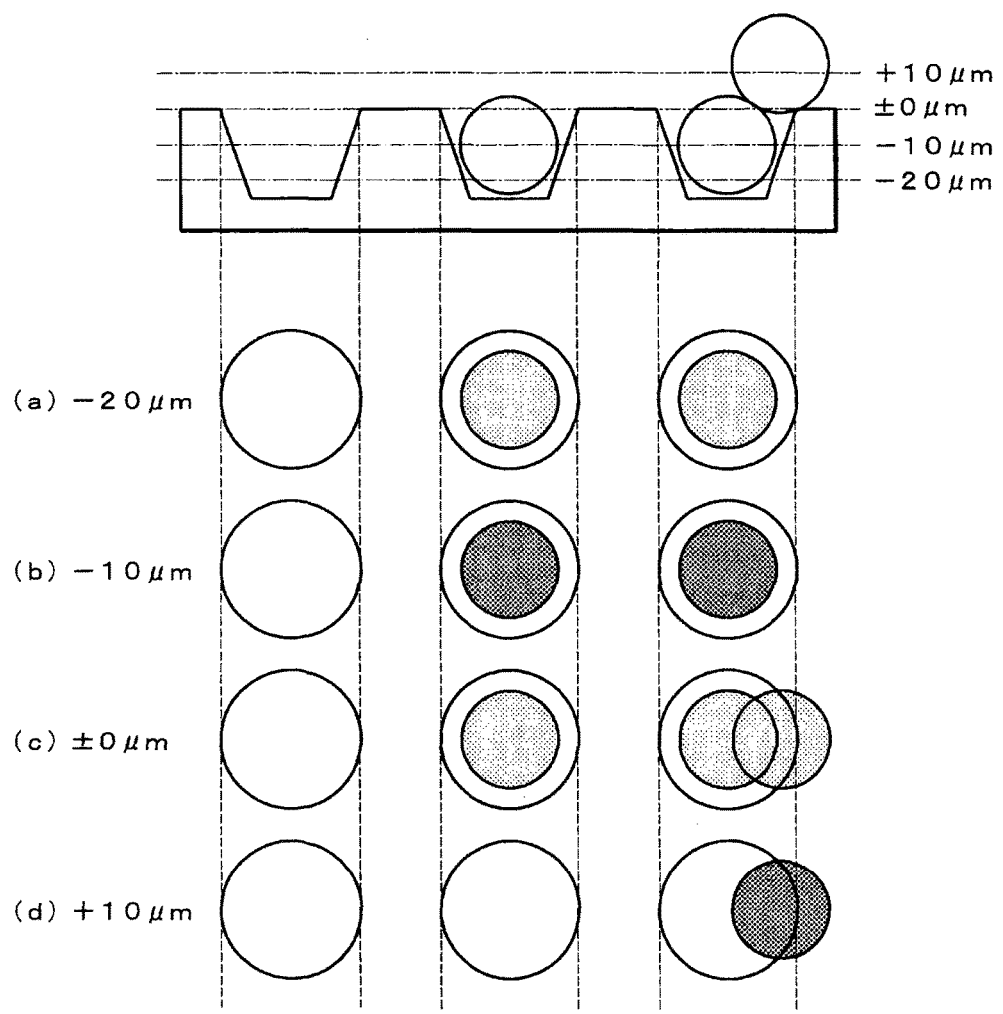
F I G. 16

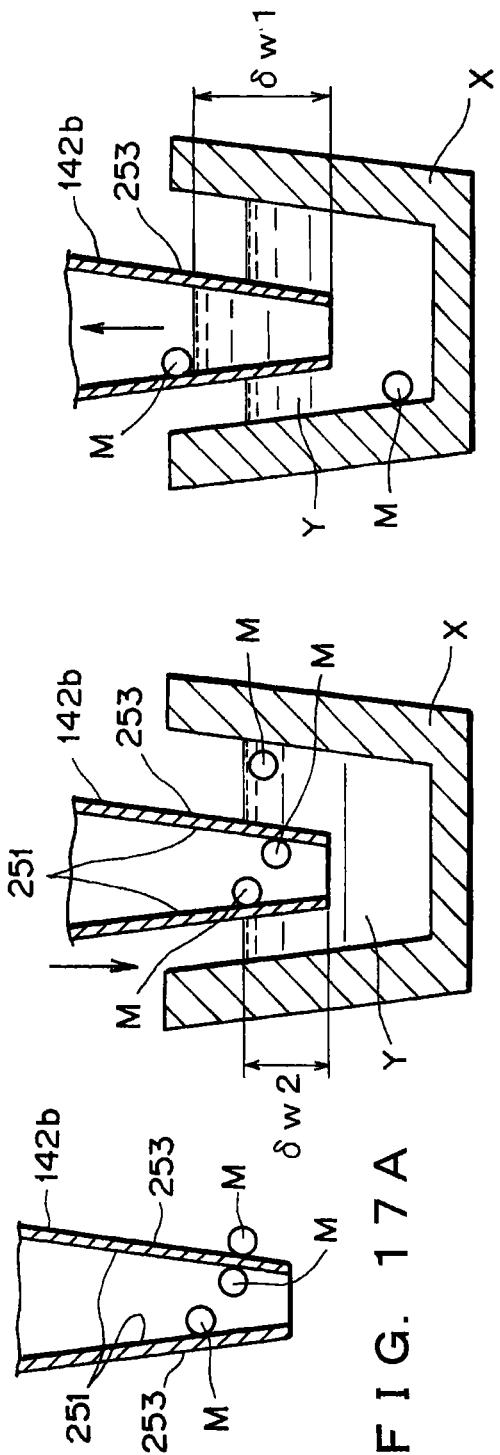

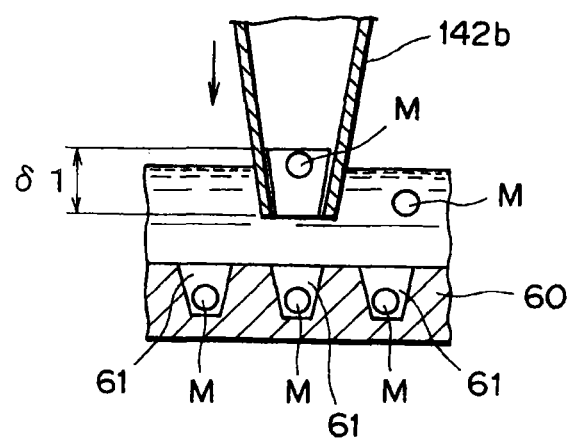
F I G. 1 8 A
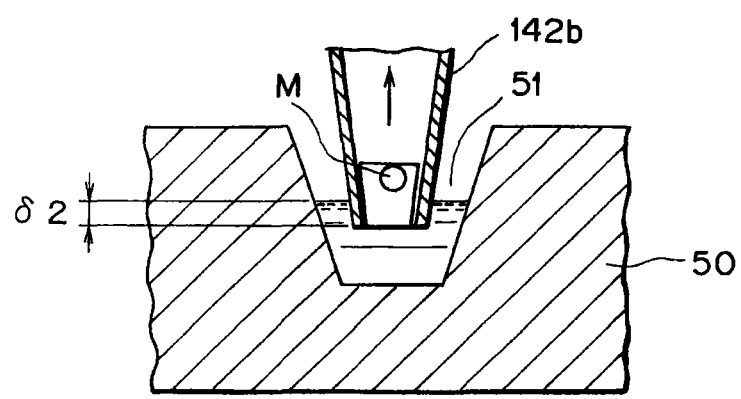
F I G. 1 8 B

SCREENING APPARATUS AND SCREENING METHOD

CROSS REFERENCE TO RELATED APPLICATIONS

This is a continuation application of International Patent Application No. PCT/JP2013/066442 filed Jun. 14, 2013, which claims the benefit of Japanese Patent Application No. 2012-224512, filed Oct. 9, 2012, the full contents of all of which are hereby incorporated by reference in their entirety.

BACKGROUND

Technical Field

The present disclosure relates to a screening apparatus and a screening method for illuminating microparticle, such as cells, detecting a microparticle to be a target sample based on fluorescence emitted from the microparticle, and selectively sucking and collecting the relevant microparticle.

Background

In the related art, microparticle screening apparatuses are widely used as apparatuses for identifying and sorting microscopic samples, such as cells, in research and testing in the medical field. Recently, in research and testing organizations, there is a need for obtaining identifying and sorting processes of the samples without fracture and for increasing efficiency of research and testing by performing those processes more accurately. Particularly, in a certain field, due to an increasing need for performing the identifying and sorting on a cell-by-cell basis, there is also a need for increasing accuracy and efficiency in the identifying and sorting processes on a cell-by-cell basis.

FIGS. 26A and 26B are diagrams for explaining an operation of a screening apparatus of the related art. FIGS. 26A and 26B show an example in which all microparticles, including a microparticle M (target sample) emitting fluorescence of a maximum luminance, are sucked from a well 501 in a measurement plate 500 and collected into a well 508 of a receiving plate 507.

In the screening apparatus of FIG. 26A, when a suction pump 504 operates in response to a command from a control unit 503, a suction-ejection capillary 505 sucks all microparticles MS, including a microparticle M emitting fluorescence of a maximum luminance, from a well 501, selectively and being distinguished from microparticles in another well 501. Thereafter, the suction-ejection capillary 505 ascends in a Z1-direction and descends in a Z2-direction to place a distal end portion 506 of the suction-ejection capillary 505 into a liquid A' in the well 508 of the receiving plate 507 and to discharge all the microparticles MS into the well 508 (FIG. 26B). In other words, all the microparticle MS can be collected from the well 501 of the measurement plate 500 with a movement operation of the measurement plate 500 in X- and Y-directions and a vertical movement operation of the suction-ejection capillary 505 in a Z-direction by a collecting section. As a result, the microparticle M which is a target sample can be detected from among a large number of microparticles and selectively collected (Japanese Laid-Open Patent Publication No. 2008-249679).

The aforementioned configuration of the related art has disadvantages described below. In a case where a large number of wells are arranged on a measurement plate, it is possible to prevent malfunctioning such as suction of a sample from a well other than the well containing a target sample. However, it merely selectively sucks all microparticles in a well containing a microparticle satisfying collecting conditions as suction target objects, and it is extremely difficult to accurately suck and collect a target sample on a cell-by-cell basis.

Further, with a shape of a distal end portion of the suction-ejection capillary and a shape of the well, or a positional relationship between them as shown in FIGS. 26A and 26B, there is a possibility that, during a suction operation, a single cell which is a target sample cannot be sucked accurately due to an influence of fluid resistance produced in the liquid in the well.

SUMMARY

It is an object of the present disclosure to provide a screening apparatus and a screening method that can accurately suck and collect a microparticle such as a cell that becomes the target sample.

In order to solve the aforementioned problem, according to an aspect of the disclosure, a screening apparatus that searches for a predetermined microparticle based on optical information emitted from microparticles to selectively pick up the microparticle searched for is a screening apparatus including a measurement chip that is made of a light permeable material, the measurement chip having a well formed therein that retains a liquid including at least one microparticle, a measuring section that acquires optical information associated with the microparticles, the optical information being obtained by illuminating the microparticles retained in the measurement chip, an analyzing section that analyzes the optical information to extract optical information associated with the microparticles retained in the well, a receiving plate that receives a microparticle selectively picked-up from the measurement chip based on a result of the analysis, a moving section that is capable of moving the measurement chip and the receiving plate with respect to the measuring section, and a collecting section having a pump and a suction-ejection capillary, the collecting section being for collecting a microparticle in the well provided in the measurement chip, the microparticle being sucked by the suction-ejection capillary and ejected at a predetermined position on the receiving plate. An outer dimension of a distal end of the suction-ejection capillary is greater than a width of the well formed in the measurement chip. The suction-ejection capillary sucks the microparticle which is a target sample at a position where the distal end of the suction-ejection capillary and the measurement chip are spaced apart by a predetermined distance and a central axis of the distal end of the suction-ejection capillary and a central axis of the well are displaced from each other.

Further, the screening apparatus includes a discharging section that discharges a liquid on the measurement chip, and an introducing section that introduces a predetermined liquid onto the measurement chip. A liquid on the measurement chip is replaced by discharging a liquid on the measurement chip by the discharging section and introducing a predetermined liquid by the introducing section.

Further, with a liquid being discharged by a predetermined amount until reaching an upper surface of the measurement chip or vicinity thereof, an arbitrary reagent may be dropped into each well.

Further, with a liquid being discharged by a predetermined amount until reaching an upper surface of the measurement chip or vicinity thereof, an arbitrary reagent may be sprayed on a predetermined region of the measurement chip.

Further, at least one partitioning portion may provided on an upper surface of the measurement chip, and a plurality of set of the discharging section and the introducing section may be provided for each of at least two regions divided by the partitioning portion.

Further, the microparticle may be contained in a single container before being retained on the measurement chip, wherein a reactant that reacts with the microparticle is added into the container for several times with a concentration of the reactant being gradually changed, and wherein a liquid in the container that contains the microparticle reacted with the reactant is introduced onto the measurement chip.

The measuring section detects a surface position of the measurement chip based on optical information related to the measurement chip which is obtained by illuminating the measurement chip, the analyzing section calculates a center position of the microparticle from the surface position and a size of the microparticle, and the measuring section illuminates a substantially center position of the microparticle retained in the well based on the center position.

Preferably, each of the wells retains one each of the microparticles, and wherein the analyzing section analyzes optical information from a single microparticle retained in each well.

The analyzing section may analyze optical information from at least one microparticle retained in each well and identifies a number of microparticles retained in each well.

Preferably, the collecting section rinses a distal end of the suction-ejection capillary before suction of the microparticle.

Preferably, a hydrophobic process surface is formed at least on an inner surface of an end portion of the suction-ejection capillary.

Further, the pump may include a tubular pump body and a plunger that is movable in a vertical direction within the pump body, and wherein the pump body includes a cylinder provided in communication with a conduit of the suction-ejection capillary and through which the plunger is movable, and a branched path provided in the cylinder.

Further, it is preferable that a valve section is connected to the branch path via a conduit, and an inner diameter of the valve section and the conduit is greater than an inner diameter of the suction-ejection capillary.

Further, it is preferable that, after the suction operation of the pump, the valve section is opened to release a residual pressure in the suction-ejection capillary.

Further, it is preferable that a displacement of the plunger at the time of ejecting the microparticle is greater than a displacement of the plunger at the time of suction of the microparticle.

Further, it is preferable that the suction-ejection capillary sucks a liquid of a predetermined amount before sucking the microparticle, and thereafter sucks the microparticle.

The collecting section further includes a detecting mechanism that detects a contact between a distal end of the suction-ejection capillary and an upper surface of the measurement chip, and a moving mechanism that adjusts a distance between the distal end of the suction-ejection capillary and an upper surface of the measurement chip, and in a case where the suction-ejection capillary is in contact with the measurement chip, the suction-ejection capillary is moved to a position where the end surface of the suction-ejection capillary and the upper surface of the measurement chip are at a predetermined distance.

Further, in order to achieve the above object, a screening apparatus that searches for a predetermined microparticle based on optical information emitted from microparticles to selectively pick up the microparticle searched for is a screening apparatus including a measurement chip that is made of a light permeable material, the measurement chip having a well formed therein that retains a liquid including at least one microparticle, a measuring section that acquires optical information associated with the microparticles, the optical information being obtained by illuminating the microparticles retained in the measurement chip, an analyzing section that analyzes the optical information to extract optical information associated with the microparticles retained in the well, a receiving plate that receives a microparticle selectively picked up from the measurement chip based on a result of the analysis, a moving section that is capable of moving the measurement chip and the receiving plate with respect to the measuring section, and a collecting section having a pump and a suction-ejection capillary, the collecting section being for collecting a microparticle in the well provided in the measurement chip, the microparticle being sucked by the suction-ejection capillary and ejected at a predetermined position on the receiving plate. An outer dimension of a distal end of the suction-ejection capillary is greater than a width of the well formed in the measurement chip. A distal end surface of the suction-ejection capillary is an inclined surface that is inclined with respect to an upper surface of the measurement chip. The suction-ejection capillary sucks the microparticle which is a target sample at a position where the distal end of the suction-ejection capillary and the measurement chip are spaced apart by a predetermined distance.

Further, in order to achieve the above objects, a screening apparatus that searches for a predetermined microparticle based on optical information emitted from microparticles to selectively pick up the microparticle searched for is a screening apparatus including a measurement chip that is made of a light permeable material, the measurement chip having a well formed therein that retains a liquid including at least one microparticle, a measuring section that acquires optical information associated with the microparticles, the optical information being obtained by illuminating the microparticles retained in the measurement chip, an analyzing section that analyzes the optical information to extract optical information associated with the microparticles retained in the well, a receiving plate that receives a microparticle selectively picked up from the measurement chip based on a result of the analysis, a moving section that is capable of moving the measurement chip and the receiving plate with respect to the measuring section, and a collecting section having a pump and a suction-ejection capillary, the collecting section being for collecting a microparticle in the well provided in the measurement chip, the microparticle being sucked by the suction-ejection capillary and ejected at a predetermined position on the receiving plate. An outer dimension of a distal end of the suction-ejection capillary is greater than a width of the well formed in the measurement chip. A horizontal sectional shape at a distal end portion of the suction-ejection capillary is non-similar to a horizontal sectional shape of the well of the measurement chip. The suction-ejection capillary sucks the microparticle which is a target sample at a position where the distal end of the suction-ejection capillary and the measurement chip are spaced apart by a predetermined distance.

A screening method of the present disclosure that searches for a predetermined microparticle based on optical information emitted from microparticles to selectively pick up the microparticle searched for is a screening method including acquiring position coordinate information of a well in the measurement chip, acquiring optical information about the microparticle by illuminating the microparticle in the well, identifying a microparticle which satisfied a predetermined collecting conditions as a target sample, based on the acquired position coordinate information and the acquired optical information, acquiring a center position of a suction-ejection capillary for sucking and ejecting the target sample, setting position which is displaced by a predetermined distance with respect to the acquired center position of the suction-ejection capillary as a center position of the well, moving the well to match the set center position, and sucking a microparticle which is the target sample at a position where an interval between a distal end of the suction-ejection capillary and the measurement chip is of a predetermined distance.

Further, in order to achieve above object, a screening apparatus that searches for a predetermined microparticle based on optical information emitted from microparticles to selectively pick up the microparticle searched for is a screening apparatus including a measurement chip that is made of a light permeable material, the measurement chip having a well formed therein that retains a liquid including at least one microparticle, a measuring section that acquires optical information associated with the microparticles, the optical information being obtained by illuminating the microparticles retained in the measurement chip, an analyzing section that analyzes the optical information to extract optical information associated with the microparticles retained in the well, a receiving plate that receives a microparticle selectively picked up from the measurement chip based on a result of the analysis, a moving section that is capable of moving the measurement chip and the receiving plate with respect to the measuring section, and a collecting section having a pump and a suction-ejection capillary, the collecting section being for collecting a microparticle in the well provided in the measurement chip, the microparticle being sucked by the suction-ejection capillary and ejected at a predetermined position on the receiving plate. The screening apparatus further includes a discharging section that discharges a liquid on the measurement chip, and an introducing section that introduces a predetermined liquid onto the measurement chip. A liquid on the measurement chip is replaced by discharging a liquid on the measurement chip by the discharging section and introducing a predetermined liquid by the introducing section.

Further, the measuring section acquires temporal variation of a fluorescence intensity of the microparticles as the optical information, and the analyzing section performs determination on the microparticle to be collected based on the optical information.

According to the present disclosure, an outer dimension of the distal end of the capillary is greater than a width of the well formed in the measurement chip, and the capillary sucks a microparticle at a position where a distal end portion thereof and the measurement chip are spaced apart by a predetermined distance and a central axis of the distal end portion and a central axis of the well are displaced with respect to each other. Thereby, microparticles are sucked and collected accurately on a cell-by-cell basis. Further, during the suction operation, since an upward one directional flow can be produced in the well, a microparticle which is a target sample can be accurately sucked without being influenced by fluid resistance produced in the liquid in the well.

BRIEF DESCRIPTION OF DRAWINGS

FIG. 5 is an enlarged sectional view showing a configuration of the measurement chip and a measurement chip securing member.

FIG. 7 a cross sectional view showing a configuration of an operating section shown in FIG. 6.

FIGS. 13A and 13B are diagrams showing a variant of a method of causing a microparticle to react in a well of the measurement chip.

FIG. 14 is a plan view showing a variant of the measurement chip.

FIG. 16 is a diagram showing, in parts (a) to (d), a focal point modification control performed by the measuring section shown in FIG. 1.

FIGS. 17A to 17C are diagrams showing a method of rinsing a distal end portion of the capillary.

FIG. 18A is a diagram showing a liquid depth in the capillary in a suction operation, and FIG. 18B is a diagram showing an insertion depth of the capillary in an ejection operation.

FIGS. 23A to 23C are diagrams showing another variant of the distal end portion of the capillary, in which FIG. 23A is a side elevation, a FIG. 23B a bottom view, and FIG. 23C is a diagram of the suction operation.

DETAILED DESCRIPTION

Further features of the present disclosure will become apparent from the following detailed description of exemplary embodiments with reference to the accompanying drawings.

Figure 1:
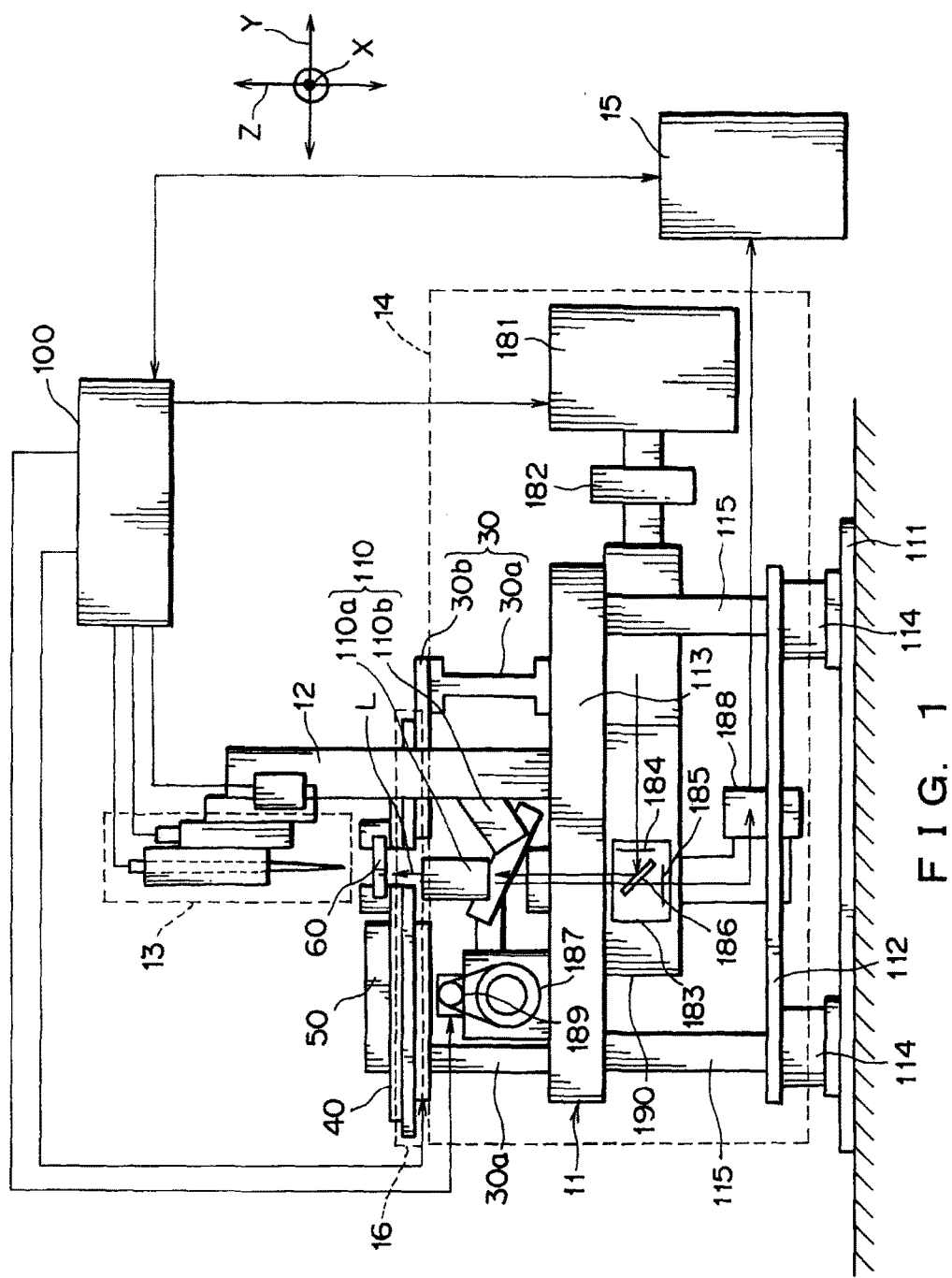
FIG. 1 is a side view schematically showing a configuration of a screening apparatus of a first embodiment of the present disclosure.
Figure 2:
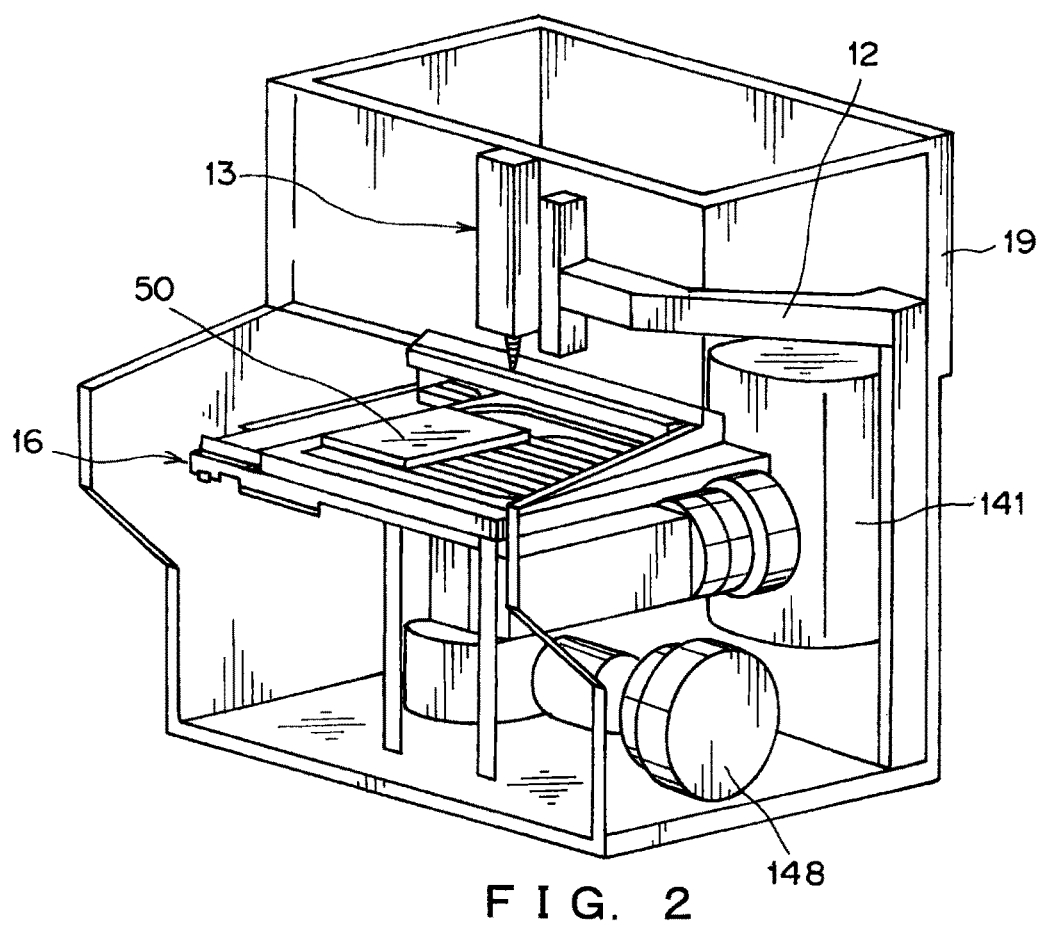
FIG. 2 is a perspective view of the screening apparatus of FIG. 1.

FIG. 1 is a side view schematically showing a configuration of a screening apparatus of a first embodiment, and FIG. 2 is a perspective view of the screening apparatus of FIG. 1.

In FIGS. 1 and 2, a screening apparatus 1 is an apparatus that illuminates a plurality of microparticles (e.g., living cells) on a measurement chip 60, searches for a predetermined microparticle to be a target sample based on fluorescence emitted from microparticles, selectively sucks microparticles in a well in which a microparticle satisfying collecting conditions is retained to collect them onto a receiving plate 50.

Specifically, the screening apparatus 1 includes a base 11, a supporting section 12 (FIG. 2), a collecting section 13, a measuring section 14, an image analyzing section 15 (analyzing section) and a moving section 16, and, as shown in FIG. 2, all the sections are covered with a cover 19. The cover 19 prevents entry of light and foreign substances from outside. The base 11 is a main body frame for holding each component of the screening apparatus 1.

As shown in FIG. 1, a direction perpendicular to the plane of paper of FIG. 1 is an X-direction (first direction) and a right and left direction is a Y-direction (second direction). Z-direction is a direction perpendicular to the X-direction and the Y-direction.

The base 11 includes plate members 111, 112 and 113 disposed substantially horizontally, and holds the collecting section 13, the measuring section 14 and the moving section 16 via the plate members. The plate members 111 and 112 are secured parallel to each other by a plurality of vertical members 114, and the plate members 112 and 113 are secured parallel to each other by a plurality of members 115. This member 115 is made of a material having a vibration shielding property and is adjustable in height.

The supporting section 12 and a supporting table 30 are secured on the plate member 113, which is located at the topmost position among the plurality of plate members. The supporting section 12 is disposed upright on the plate member 113 vertically and along Z-direction. The supporting table 30 includes leg sections 30a and a support-plate 30b. The plate members 111, 112 and 113 and the support-plate 30b are disposed at a predetermined interval between each other in the Z-direction.

The moving section 16 is mounted and secured on the support-plate 30b of the supporting table 30. A mounting table 40, a receiving plate 50 and a measurement chip 60 are mounted on the moving section 16. The moving section 16 is capable of moving and positioning the mounting table 40, i.e., the receiving plate 50 and the measurement chip 60, along the X-direction and/or the Y-direction.

Figure 3:
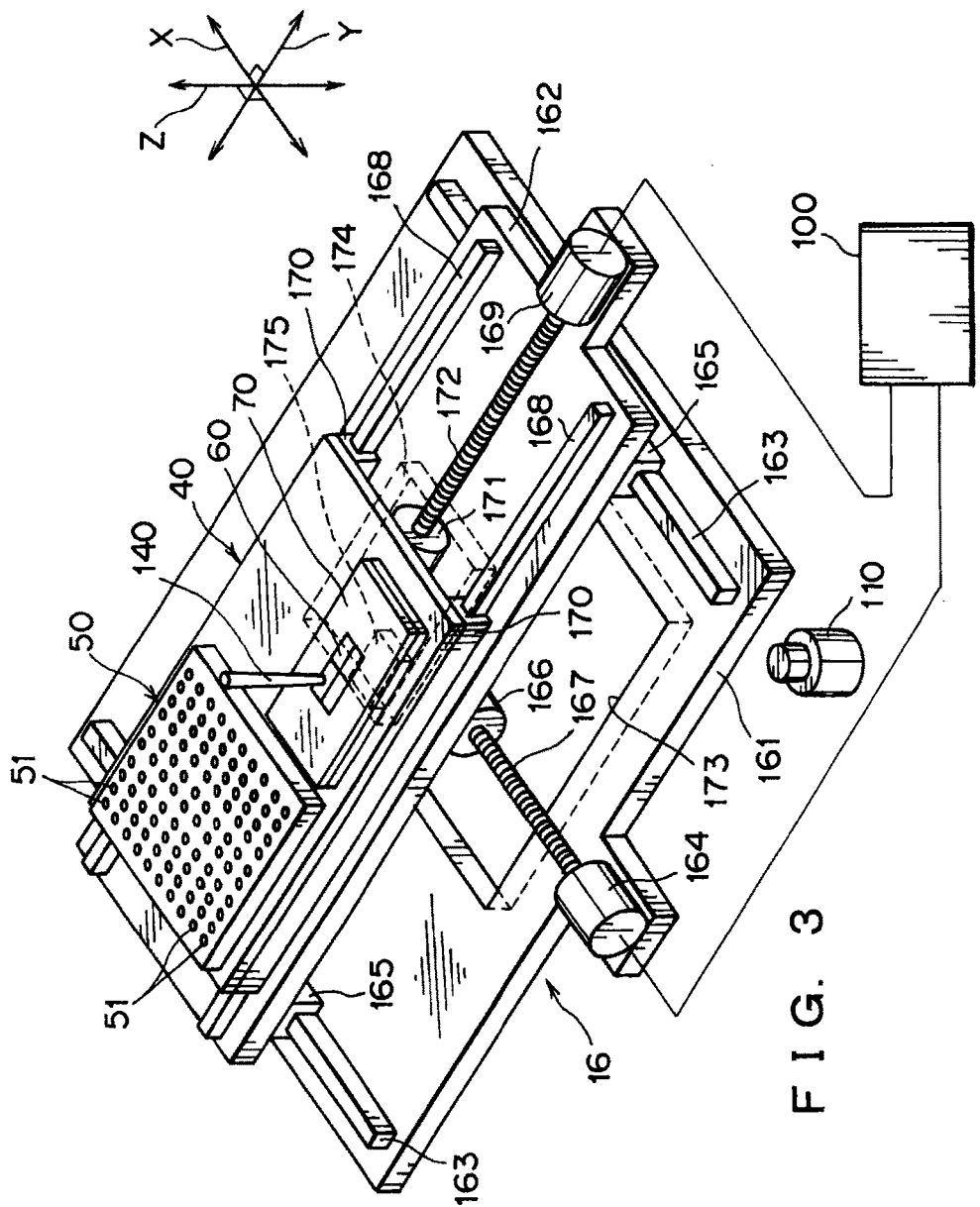
FIG. 3 is a perspective view showing details of a moving section and a mounting table shown in FIG. 2.

FIG. 3 is a perspective view showing details of the moving section 16 and the mounting table 40 shown in FIG. 2.

As shown in FIG. 3, the moving section 16 includes a table 161 and a table 162 disposed on the said table. The table 161 is secured to the supporting table 30, and the table 162 mounted thereon can be positioned by being moved along the X-direction. On the table 162, the mounting table 40 is mounted so as to be capable of being positioned by being moved along the Y-direction.

Guide rails 163 and 163 and a motor 164 are provided on an upper surface of the table 161. Engaging members 165 and 165 each having a U-shaped cross section and a nut 166 are provided on a lower surface of the table 162. The engaging members 165 and 165 movably engage with the guide rails 163 and 163, respectively. A feed screw 167 of the motor 164 is screwed to the nut 166.

The motor 164 is electrically connected to a control unit 100. By operating the motor 164 in response to a command from the control unit 100 to rotate the feed screw 167, the table 162 is positioned by being moved along the X-direction.

Guide rails 168 and 168 and the motor 169 are provided on an upper surface of the table 162. Engaging members 170 and 170 each having a U-shaped cross section and a nut 171 are provided on a lower surface of the mounting table 40. The engaging members 170 and 170 movably engage with the guide rail 168 and 168, respectively. A feed screw 172 of the motor 169 is screwed to the nut 171.

The motor 164 is electrically connected to the control unit 100. By operating the motor 164 in response to a command from the control unit 100 to rotate the feed screw 172, the mounting table 40 is positioned by being moved along the Y-direction.

The tables 161 and 162 have openings 174 and 173, respectively, and further, the mounting table 40 includes an opening 175. These openings 173, 174 and 175 have respective sizes that they always overlap with each other even if the table 162 moves in the X-direction and the mounting table 40 moves in the Y-direction. Through these openings 173, 174 and 175, light L from an objective lens 110 side of the measuring section 14 is illuminated on the microparticles on the measurement chip 60 on the mounting table 40.

Also, even if the table 162 has moved in the X-direction and the mounting table 40 has moved in the Y-direction, light L from the objective lens 110 side passes through the opening 173, 174 and 175 and is illuminated on microparticles on the measurement chip 60 on the mounting table 40. That is, fluorescence can be produced from microparticles at any relative position between the tables 161, 162 and the mounting table 40.

Figure 4:
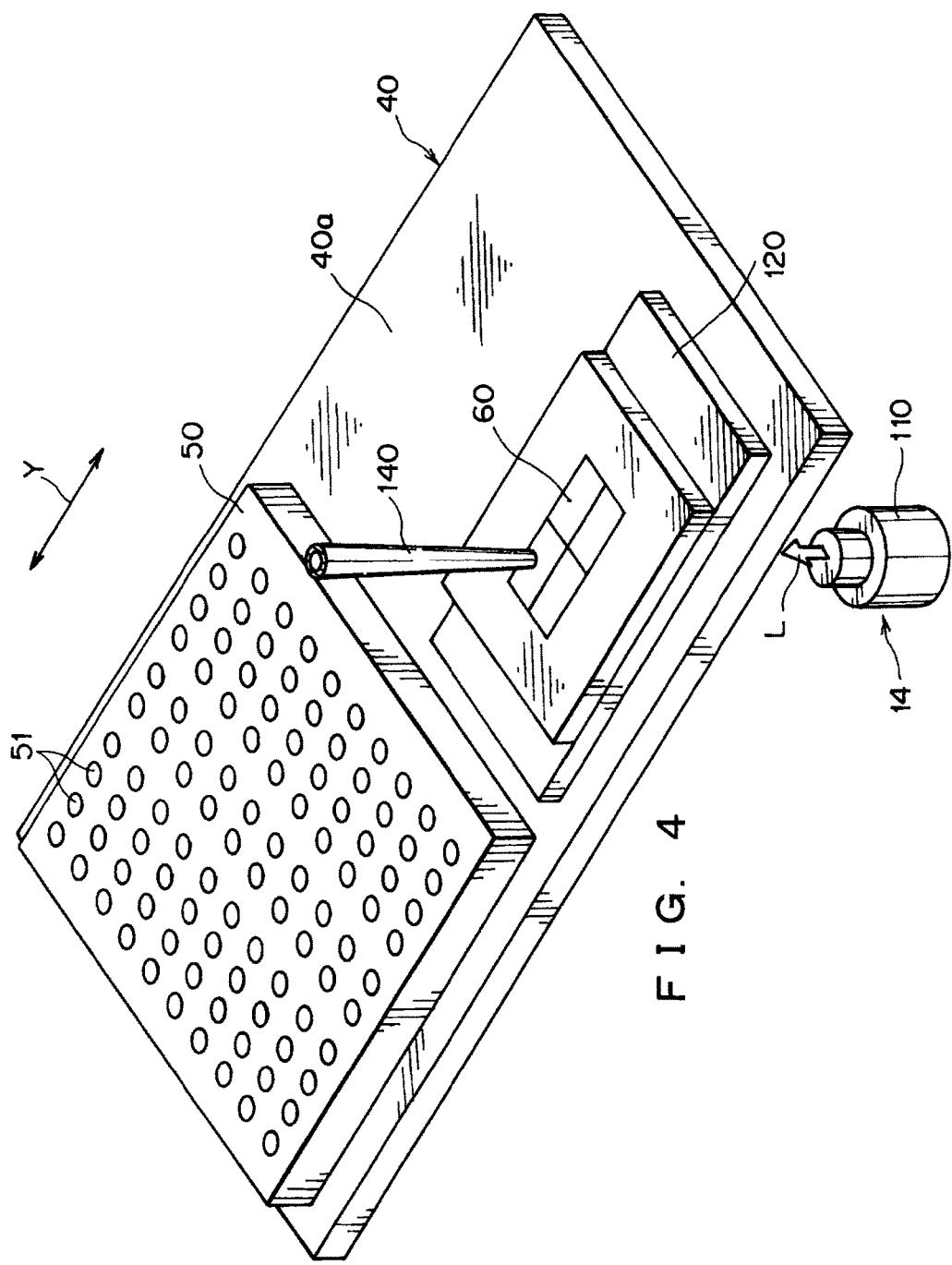
FIG. 4 is a perspective view showing a configuration of a receiving plate and a measurement chip on the mounting table shown in FIG. 3.

FIG. 4 is a perspective view showing a configuration of the receiving plate 50 and a measurement chip 60 on the mounting table 40 shown in FIG. 3.

The mounting table 40 is, for example, a rectangular plate-like member. The receiving plate 50 and the measurement chip 60 can be detachably mounted on a mounting surface 41 of the mounting table 40 so as to be arranged along the Y-direction.

The receiving plate 50 is a plate-like member. The receiving plate 50 includes a large number of wells 51 arranged in a matrix at a constant interval along the X-direction and the Y-direction. The wells 51 are collecting-and-storing sections each capable of, when microparticles such as organism cells are discharged sequentially from a suction-ejection capillary 140, separately collecting and storing microparticles which have been discharged sequentially. For example, the well 51 of the receiving plate 50 is a recessed portion having, for example, a substantially U-shaped vertical direction cross section or a recessed portion having a cup-shape.

The measurement chip 60 is secured to a mounting surface 40a of the mounting table 40 by a securing member 120, and the fixing member 120 is positioned and secured at a predetermined position on the mounting table 40.

FIG. 5 is an enlarged sectional view showing a configuration of the measurement chip 60 and the securing member 120 of the measurement chip. The securing member 120 secures and holds the measurement chip 60 at a position of a reference level CL at a certain level with respect to the mounting surface 41 of the mounting table 40. Specifically, the securing member 120 includes casing sections 121, 122 and an elastic member 123. For example, the elastic member 123 is a substantially rectangular ring member, and the elastic member 123 is secured to a flat surface 126 inside the casing section 122.

The measurement chip 60 is placed between the casing sections 121 and 122, and with the measurement chip 60 being pushed up in the Z1 direction by an elastic member 123, an upper surface 60a of the measurement chip 60 is in pressure contact with a flat inner lower surface 121a of the casing section 121. Further, the inner lower surface 121a of the casing section 121 is provided with a sealing member 128, and the sealing member 128 provides a seal between the reference level CL of the securing member 120 and the upper surface 60a of the measurement chip 60.

With the upper surface 60a of the measurement chip 60 being pressed against the inner lower surface 121a of the casing section 121, the upper surface 60a of the measurement chip 60 is positioned to the reference level CL. Thereby, even if there is, for example, a thickness variation and warping of the measurement chip 60, it is possible to reduce a decrease in an accuracy of positioning due to an influence of the thickness variation and an influence of the warping. Therefore, a distance in the Z-direction between the upper surface 60a of the measurement chip 60 from an objective lens 110 of the measuring section 14 and the receiving plate 50 can be controlled accurately. In other words, a position of a microparticle M in the well 61 of the measurement chip 60 and the distance between the objective lens 110 of measuring section 14 and the receiving plate 50 can be managed accurately.

Further, the casing section 121 includes a liquid holding section 129 that retains a liquid A, which is provided at a central part in a direction of its plane and above the measurement chip 60, and is capable of retaining various liquids such as a medium, a reagent, and a reaction liquid. The casing section 121 can be opened and closed with respect to the casing section 122 using, for example, a hinge assembly section, not shown. Thereby, the measurement chip 60 in the securing member 120 can be removed and replaced with a new measurement chip 60.

The measurement chip 60 is made of a translucent material, e.g., glass and plastics, and, a large number of wells 61 are arranged in a matrix in the upper surface 60a thereof. For example, each of the wells 61 is a recessed portion having a substantially a trapezoid or a substantially cup-shaped vertical cross section, and a horizontal cross section of the well 61 is preferably substantially circular. It has such a size that a single microparticle M can be stored therein by dispensing or batch-introducing the microparticles M.

Figure 6:
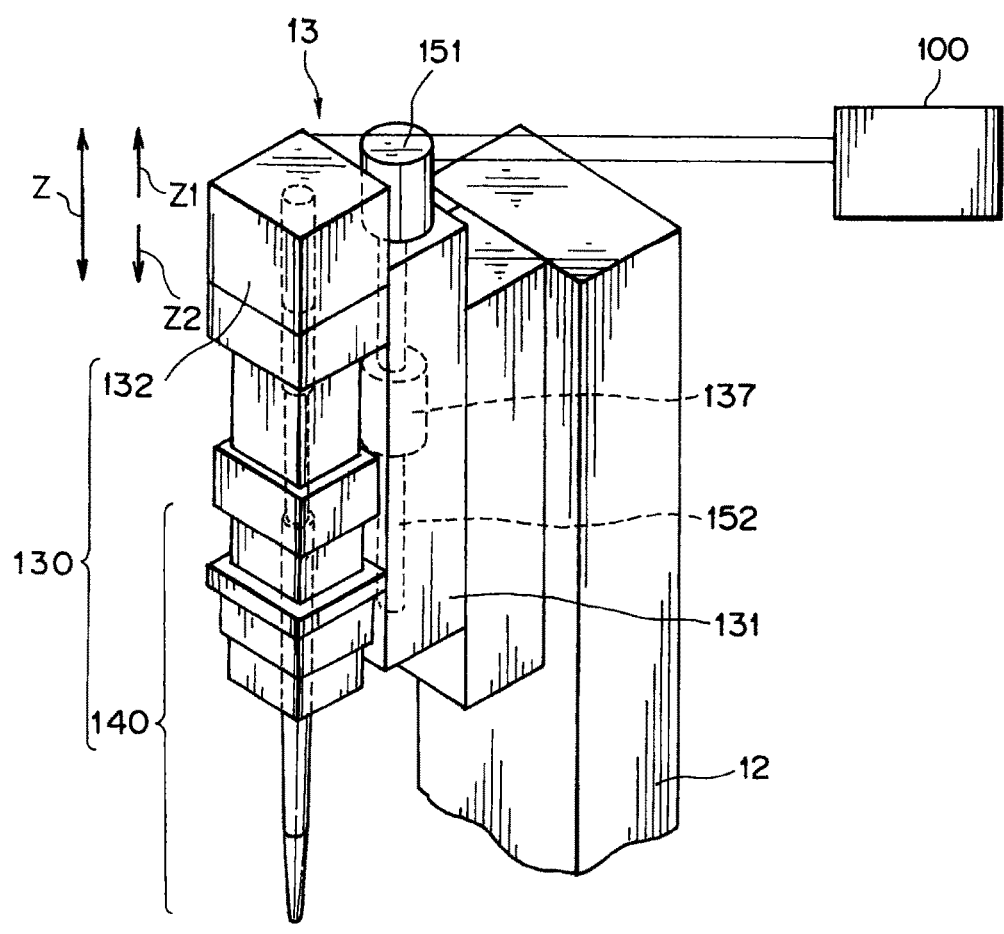
FIG. 6 is a perspective view showing a configuration of a collecting section shown in FIG. 1.

FIG. 6 is a perspective view showing a configuration of a collecting section 13 shown in FIG. 1, and FIG. 7 is a cross sectional view showing a configuration of the operating section shown in FIG. 6. The collecting section 13 includes an operating section 130 and a base section 131, and the base section 131 is secured to the supporting section 12. The operating section 130 includes an actuator 132 (pump) and a suction-ejection capillary 140.

The actuator 132 includes an actuator main body 133, and a substantially cylindrical plunger 136 accommodated in a cylinder 134 of the actuator main body 133, and a predetermined fluid is pumped with a reciprocating plunger 136 within the cylinder 134. A conduit 135 that provides communication between the cylinder 134 of the actuator main body 133 and the suction-ejection capillary 140 is provided below the actuator 132.

The suction-ejection capillary 140 includes a flange section 141 that is detachably attached to the conduit 135 and a capillary main body 142 (hereinafter, simply referred to as a "capillary") that is penetrating through the flange section 141 and extending downwardly. At a connection surface between the flange section 141 and the conduit 135, a ring-shaped elastic member 143 is attached. When the flange section 141 is attached, with the elastic member 143 being secured and pressed, a proximal end portion of the capillary 142 to be described below is sealed and connected with the conduit 135.

The capillary 142 is a hollow member having a tapered shaped with its diameter decreasing along the Z2 direction (downward direction) and has a conduit formed therethrough. A proximal end portion 142a of the capillary 142 is connected to the conduit 135. A distal end portion 142b of the capillary 142 is in the vicinity of the well 61 of the measurement chip 60 during the suction of a microparticle.

The base section 131 includes a motor 151 disposed at an upper end of the base section and a feed screw 152 attached to the motor, and the feed screw 152 is screwed to a nut 137 of the operating section 130. The motor 151 is electrically connected to the control unit 100. The control unit 100 operates the motor 151 to rotate the feed screw 152 to thereby vertically move and position the operating section 130 together with the nut 137 along the Z-direction (Z1 and Z2 directions).

By illuminating light L onto a region of the measurement chip 60 in which a plurality of wells 61 are provided, the measuring section 14 causes fluorescence to be produced from microparticles M in the region and receives the fluorescence (FIG. 1). The fluorescence received from the microparticles M is subjected to an image analysis by an image analyzing section 15. The image analyzing section 15 calculates a fluorescence intensity (luminance) of a microparticle M1 emitting fluorescence of at least a maximum luminance from among a plurality of microparticles M in each well 61.

The control unit 100 detects, in a plane constituted by an X-direction and a Y-direction, a position of the well 61 in which the microparticle M1 emitting fluorescence of a maximum luminance satisfying the collecting conditions is contained. Then, by supplying a control driving signal to the motors 164 and 169 of FIG. 3, the control unit 100 can position the well 61 of the measurement chip 60 on the moving section 16 directly beneath the suction-ejection capillary 140. That is, the suction-ejection capillary 140 is configured to be capable of targeting a particular well and sucking a microparticle in the well. Further, the suction-ejection capillary 140 can suck, from a selected well among a plurality of wells, in other words, from a well containing a microparticle satisfying predetermined collecting conditions, at least one microparticle. Further, the suction-ejection capillary 140 can eject the selected at least one microparticle into a predetermined well 51 in the receiving plate 50.

By illuminating the measurement chip 60 and microparticles M retained in the measurement chip 60 with light guided from at least one light source, the measuring section 14 acquires shape and position information obtained from transmitted light, reflected light or fluorescence, and luminance information such as chemiluminescence with a resolution finer than an average size of the microparticles, and also acquires information such as a shape of the measurement chip itself or a positional coordinate or a size of the well 61 disposed in the measurement chip 60.

By analyzing the measured shape information and optical information, the image analyzing section 15 acquires data for confirming that a microparticle M1 satisfying an luminance condition which can be set by the observer exists at least in each well 61. The image analyzing section 15 extracts optical information from the microparticles by matching and verifying the positional coordinate information of the well 61 from the transmitted light or the reflected light, and the optical information of fluorescence and chemiluminescence. Further, the measuring section 14 has an autofocus function. The measuring section 14 is capable of performing measurement while being focused at a predetermined position and determining a positional relationship between the distal end portion 142b of the suction-ejection capillary 140 and an upper surface of the measurement chip 60 by performing an autofocus on both of them.

Further, the measuring section 14 has an objective lens 110, and the objective lens 110 guides light to the measurement chip 60. The objective lens 110 is disposed below the measurement chip 60 and the moving section 16, and the suction-ejection capillary 140 is disposed above the measurement chip 90 and the moving section 16. Accordingly, the measurement chip 90 and the moving section 16 thereof can be disposed between the objective lens 110 and the suction-ejection capillary 140.

Concerning the measuring section 14, a pump light source 181 includes, for example, a laser source and a mercury lamp. A shutter unit 182 is disposed between the pump light source 181 and a fluorescence filter unit 183. The shutter unit 182 is capable of blocking light L produced by the pump light source 181 directly in front of the fluorescence filter unit 183 in a case where the light L is not illuminated on the microparticles M on the measurement chip 60.

Specifically, the measuring section 14 includes the pump light source 181 as a light source, the fluorescence filter unit 183 comprising an optical filter (pump filter) 184 for selecting only a desired pump wavelength band among light illuminated from the pump light source 181, an optical filter (fluorescence filter) 185 for selecting only a desired wavelength band of the optical information from the measurement chip 60, and a dichroic mirror 186 for changing an optical path length in accordance with a difference between wavelength bands of the pump light and the optical information. Further, the measuring section 14 has the objective lens 110 for guiding light emitted from the pump light source 181 to the measurement chip 60 and for collecting optical information obtained from the measurement chip 60, a focus unit 187 having an automatic focus function capable of moving the objective lens 110 in an optical axis direction, and a light receiving section 188 as an optical information from a measurement object. The fluorescence filter unit 183 and the light receiving part 188 are fixed to an epifluorescence unit 190.

Further, the measuring section 14 includes a half mirror, not shown. By switching between the half mirror and the fluorescence filter unit 183, a part of the light from the pump light source 181 is irradiated on an observation target, and at the same time, a part of the reflected light from the observation target is guided to a light receive part 188. Thereby, shape and position information of the upper surface 60a of measurement chip 60 and the well 61 formed on the upper surface can be measured.

In this measuring section 14, by rotating a plurality of objective lens 110a, 110b . . . , for example, in a revolver manner, an objective lens of a required magnification can be positioned at a position below the measurement chip 60. By operating the motor 189 in accordance with, for example, a command from the control unit 100, the objective lens 110, for example, located at a position below the measurement chip 60 is moved and positioned along the Z-direction, the focus unit 187 can perform focus adjustment of the objective lens 110 on microparticles M in the measurement chip 60.

Concerning the screening apparatus 1 configured as above, the present inventors focused their attention on the capillary 142 and the measurement chip 60, and particularly on their positional relationship and sizes during the suction, and found that the collecting section 13 can accurately suck the microparticles M on the measurement chip 60. Hereinafter, a detailed description will be made with reference to FIGS. 8 and 9.

Figure 8:
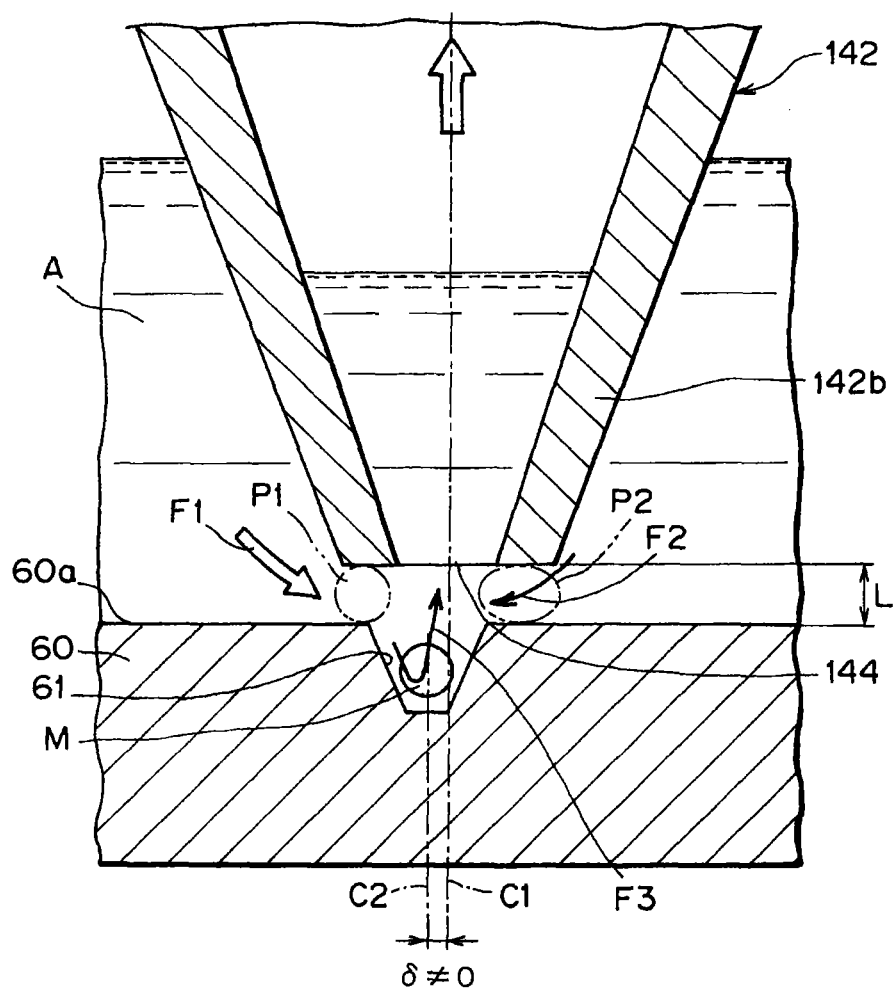
FIG. 8 is a cross sectional view showing a positional relationship between a capillary and a well during suction of a microparticle.
Figure 9:
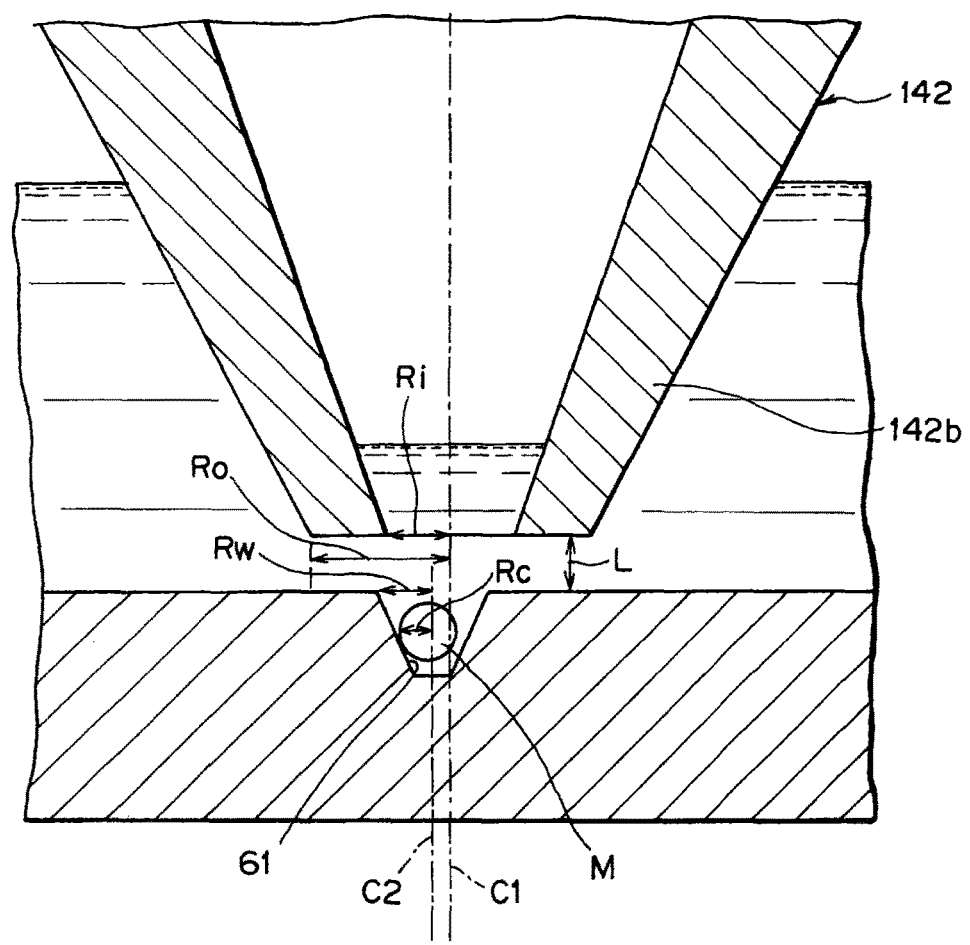
FIG. 9 is a diagram for explaining conditional expressions defined using dimensions of the capillary, the well and the microparticle, and a distance between the capillary and the measurement chip.

FIG. 8 is a cross sectional view showing a positional relationship between the capillary 142 and the well 61 during suction of a microparticle.

Firstly, as shown in FIG. 8, the distal end portion 142b of the capillary 142 has a substantially annular cross section and has an end surface 144. An outer dimension of the distal end of the capillary 142 is designed to be greater than a width of the well 61 formed in the measurement chip 60. By placing the end surface 144 and the upper surface 60a of the measurement chip 60 at a distance L (L>0), a flow path leading into the capillary 142 is formed between the end surface 144 and the upper surface 60a during the suction operation. In the present embodiment, the capillary 142 is disposed in such a manner that a central axis C1 of the capillary 142 is displaced from a central axis C2 of the well 61. In other words, the distance between the central axis C1 of the capillary 142 and the central axis C2 of the well 61 is $\delta$ ($\delta \neq 0$). At this time, a flow path P1 and a flow path P2 longer than the flow path P1 are formed between the end surface 144 and the upper surface 60a. When the capillary 142 sucks a liquid A with this positional relationship, a liquid flow F1 is produced in a flow path P1 and a liquid flow F2 of a flow rate smaller than the liquid flow F1 is produced in a flow path P2. Due to the liquid flows F1 and F2 thus produced which are different from each other, an upward one way flow F3 is produced in the well 61, and a microparticle M is lifted upward from within the well 61 due to this one way flow F3. With this action, an accurate suction of a microparticle M using the capillary 142 is achieved.

Also, in the positional relationship described above, when the distance L between the capillary and the measurement chip, and dimensions of the capillary 142, the well 61 and the microparticle M satisfy predetermined conditions, a more accurate suction operation can be achieved. For example, in the present embodiment, assuming that the distal end portion 142b of the capillary 142 has a substantially cylindrical shape, and by letting Ro be an outer peripheral radius of the distal end portion 142b, Ri be an inner peripheral radius of the distal end portion 142b, Rw be an aperture radius of the well 61, and Rc be a radius of the microparticle M, it is designed to satisfy the following three conditional expressions (1) to (3) shown below.

$$2Rc \geq L \tag{1}$$

$$Ro-Ri \geq 0.5L \tag{2}$$

$$Ro-Rw \geq 0.5L \tag{3}$$

Specific dimensions satisfying the conditional expressions of (1) . . . (3) are shown in Table 1.

TABLE 1

|  | Rc | Rw | Ri | Ro | EXPRESSION 1 | EXPRESSION 2 | EXPRESSION 3 | CONDITIONS SATISFYING EXPRESSIONS 1 TO 3 |
|---|---|---|---|---|---|---|---|---|
| EXAMPLE 1 | 2.5 | 5 | 8 | 15 | $5 \geq L$ | $14 \geq L$ | $20 \geq L$ | $5 \geq L$ |
| EXAMPLE 2 | 5 | 10 | 10 | 17.5 | $10 \geq L$ | $15 \geq L$ | $15 \geq L$ | $10 \geq L$ |
| EXAMPLE 3 | 7 | 10 | 12.5 | 22.5 | $14 \geq L$ | $20 \geq L$ | $25 \geq L$ | $14 \geq L$ |
| EXAMPLE 4 | 8 | 15 | 15 | 22.5 | $16 \geq L$ | $15 \geq L$ | $15 \geq L$ | $15 \geq L$ |
| EXAMPLE 5 | 10 | 15 | 16.5 | 22.5 | $20 \geq L$ | $12 \geq L$ | $15 \geq L$ | $12 \geq L$ |

As has been described above, in the present embodiment, the distance L between the capillary 142 and the well 61 is smaller than a diameter of the microparticle M (2Rc) (conditional expression (1)). By satisfying this condition, microparticles M retained in adjacent other wells 61 will not be sucked. Also, a value obtained by subtracting the inner peripheral radius Ri of the capillary 142 from the an outer peripheral radius Ro is greater than a half of the distance L (conditional expression (2)), and further, a value obtained by subtracting the aperture radius of the well 61 from the outer peripheral radius Ro of the capillary 142 is greater than a half of the distance L (conditional expression (3)). By satisfying these two conditions, the one way flow F3 for sucking a microparticle M can be positively produced. Therefore, a further accurate suction operation of a microparticle M is achieved satisfying the three conditional expressions described above.

It is preferable that the distance b between the central axis C1 and the central axis C2 is, for example, about 0.1 times to 1 time of the aperture radius Rw of the well 61. With such a configuration, the upward one way flow F3 can be produced easily. Also, it is more preferable that the distance b is about 0.2 times to 0.4 times the aperture radius Rw of the well 61. Thereby, the microparticle M can be smoothly collected with the capillary 142.

Concerning the relationship between an inner diameter of the capillary 142 and the outer diameter of the well 61 of the measurement chip, it is preferable that the inner peripheral radius Ri of the capillary is about 0.8 times to 2 times the aperture radius Rw of the well 61.

In the suction operation by the capillary 142, in addition to defining the positional relationship and dimensions described above in the suction, it is more effective to perform a pre-suction operation which sucks a specific amount of liquid A before sucking a microparticle M. The suction control including this pre-suction operation is performed by the collecting section 13 and the control unit 100.

Figure 10:
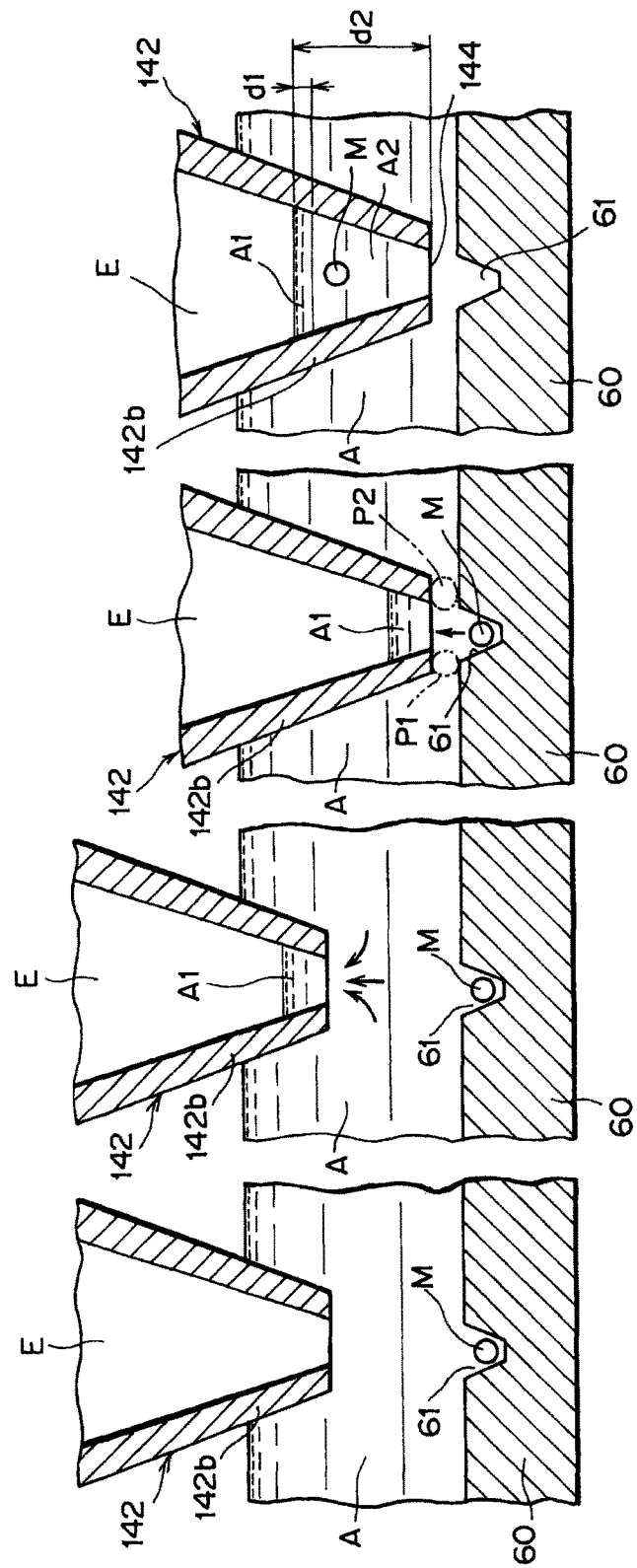
FIGS. 10A to 10D are diagrams for explaining suction control performed by the collecting section.

Firstly, the distal end portion 142b of the capillary 142 is inserted into the liquid A retained on the measurement chip 60 (FIG. 10A). Then, when the distal end portion 142b is inserted into the liquid A to a predetermined depth to such an extent that it does not influence the liquid in the well 61, a pre-suction operation is performed for a predetermined period of time. At this time, a specific amount of liquid A enters into an inner space E of the capillary 142, and a liquid layer A1 is formed in the distal end portion 142b of the capillary 142 (FIG. 10B). Thereafter, the capillary 142 is made to approach the measurement chip 60 to such a position where the distance is L as described above (FIG. 10C). When the suction operation is performed for a predetermined period of time, a specific amount of liquid A enters the distal end portion 142b of the capillary 142, and a microparticle M in the well 61 enters into the distal end portion 142b together with the specific amount (FIG. 10D). Thereby, a liquid layer A2 is formed in the distal end portion 142b of the capillary 142, and the microparticle M which is a target sample is sucked into the capillary 142.

In this suction control, as shown in FIG. 10D, by letting d1 be a depth of the liquid layer A1 and d2 be a depth of the liquid layer A1+A2, it is preferable that the following conditional expression is satisfied.

$$d1/d2 \geq 0.1 \quad (4)$$

For example, when a capillary having an inner diameter of the end surface 144 of the distal end portion 142b of 30 μm and a taper angle of 10° is used and a total amount of sucked liquid until suction of the microparticle M is set at 1 the aforementioned d1 is 0.3 mm and d2 is 2.7 mm. Therefore, an amount of liquid of the liquid layer A1 formed by the pre-suction operation is 0.3 μl, and an amount of liquid of the liquid layer A2 formed by a subsequent suction operation (microparticle suction operation) is 0.7 μl.

By performing such a suction control, the liquid layer A1 is formed within the capillary 142 before the capillary 142 arrives at a position to start suction of a microparticle M. Thus, even if a microparticle M is sucked immediately after the suction operation has started, the microparticle M will not be placed at a liquid surface in the capillary 142, and the liquid layer A1 will be placed upwardly of the microparticle M. In an ejection operation of the capillary 142, since the liquid layer A1 presses the microparticle M downwardly, the microparticle M does not remain in the capillary 142. Specifically, a phenomenon such as the microparticle M remains by being attached to an inner wall of the capillary 142 is prevented, and an ejection accuracy of the microparticle M improves.

Note that, in the pre-suction operation described above, the capillary 142 may suck from any another container containing any liquid, and this liquid may be different from the liquid A. In order to improve accuracy of observation and analysis, it is preferable to select and use a liquid having a weak self-fluorescence as the liquid A. However, it is not necessarily advantageous to the microparticle. For example, by pre-sucking the same liquid as the liquid which is received in the receiving plate 50 in advance, it is possible to minimize the liquid A brought onto the receiving plate 50.

A screening method of the target sample of the present disclosure will now be described.

Figure 11:
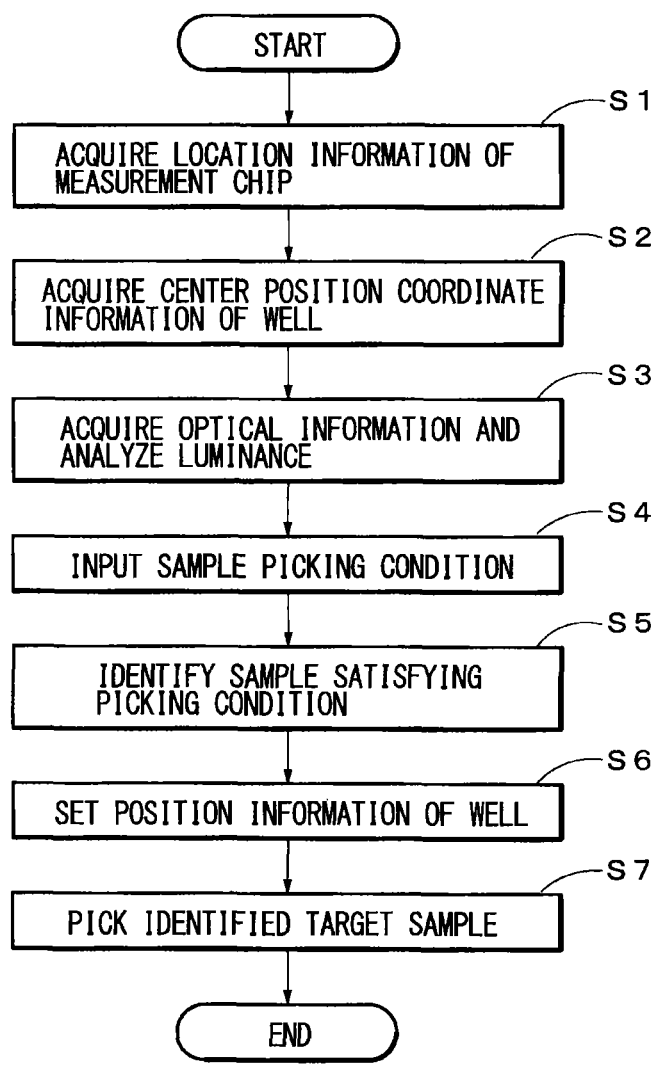
FIG. 11 is a flow chart for explaining a method of screening a target sample in the present disclosure.
Figure 15A:
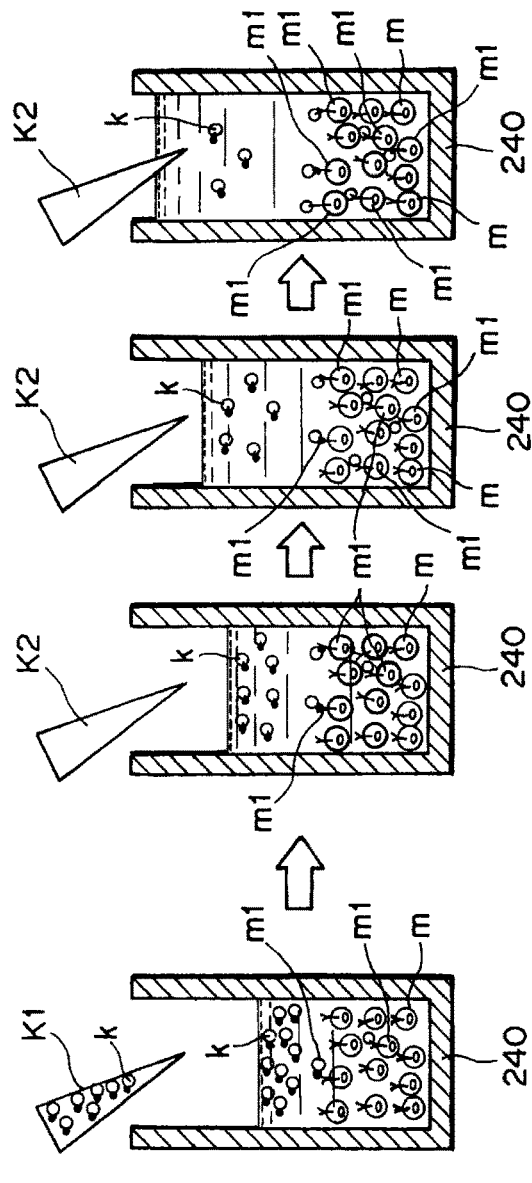
FIGS. 15A and 15B are diagrams for explaining a method of causing a microparticle to react in a single container before being retained on the measurement chip.
Figure 15B:
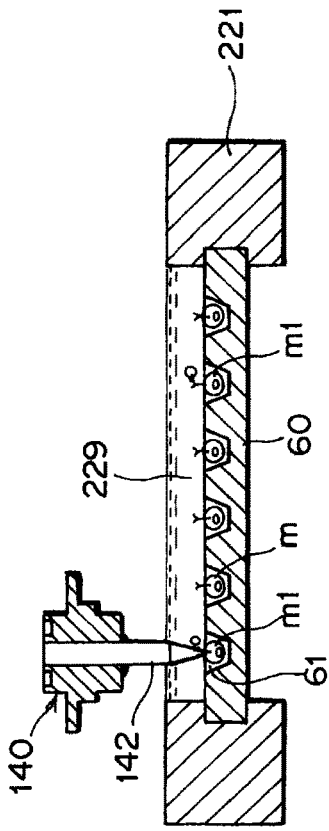

As shown in FIG. 11, firstly, location information of the measurement chip 60 is acquired from information regarding a reference position of the measurement chip and correction parameters or the like (step S1). Thereafter, an image analysis is performed to acquire center position coordinate information of each well (step S2). Then, a light is illuminated to acquire optical information of a microparticle (sample) and a luminance analysis is carried out (step S3). The luminance analysis may be performed by, for example, as shown in FIG. 12D described later, introducing a reaction liquid into each of the wells to cause the microparticles in the well to produce fluorescence, and measuring a temporal variation of this fluorescence information. Also, as shown in FIGS. 15A and 15B described later, the microparticles stored in each well on the measurement chip 60 may be counted.

Then, based on the acquired fluorescence information, collecting conditions may be set as collecting conditions of a microparticle required by a user, for example, conditions in which a luminance of a certain fluorescence has exceeded a predetermined threshold, or a condition in which, when a plurality of fluorescence (e.g., colors of the fluorescence are different) are used, a luminance of at least one of the fluorescence has exceeded a predetermined threshold, or any combination thereof. Alternatively, for a luminance of any fluorescence, conditions to be excluded from collecting (the one which is lower than a threshold) may be combined. Some conditions determined in a manner described above are input (step S4), and a microparticle that satisfies the aforementioned collecting conditions is identified as a target sample (step S5). Then, a center position of the capillary is acquired by an image analysis, and a position shifted towards the center position by a distance δ is set as a center position of the well during the collecting of the microparticle (position information) (step S6). The center position of each of the wells in which a target sample is contained is moved to match the center position of the well during the collecting of the microparticle, which is set in step S6, and target samples identified in step S5 are collected sequentially (step S7). The collected sample is placed in a predetermined well in the receiving plate 50 which was set in advance by the user.

As has been mentioned above, according to the present embodiment, an outer dimension of the distal end of the capillary 142 is greater than a width of the well 60 formed in the measurement chip 60, and the capillary 142 sucks a microparticle M at a position where an interval between the distal end portion 142b and the measurement chip 60 is distance L and the central axis C1 of the distal end portion 142 and the central axis C2 of the well 61 are at positions displaced from each other. Thereby, a microparticle M can be accurately sucked and collected on a cell-by-cell basis. Also, in the suction operation, since an upward one-way flow F3 is produced within the well 61, a microparticle M, which is a target sample, can be accurately sucked without being influenced by a fluid resistance produced in the liquid A in the well 61. Further, with the aforementioned configuration, a single microparticle M which is a target sample can be accurately sucked and collected, and a process can be performed on a cell-by-cell basis.

A screening apparatus of the second embodiment will be described below. The screening apparatus of the present embodiment includes the screening apparatus of the first embodiment and additionally a mechanism of introducing a liquid into a liquid holding section and discharging the liquid from the liquid holding section. It is to be noted that the second embodiment does not necessarily include the configuration of the screening apparatus of the first embodiment, and may be implement independently, without depending on the configuration of the first embodiment.

Figure 12A:
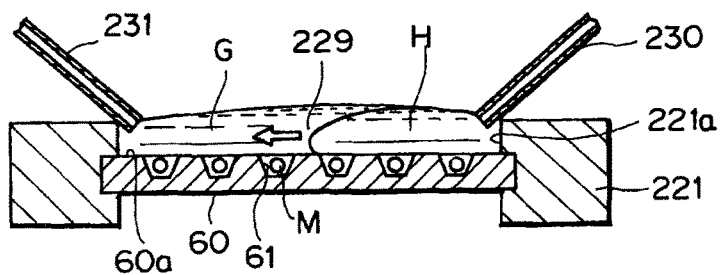
FIGS. 12A to 12C are diagrams showing a schematic configuration of a liquid discharging section and a liquid introducing section that are provided in the vicinity of a measurement chip in a screening apparatus of a second embodiment.

In this screening apparatus, as shown in FIG. 12A, a casing section 221 has a liquid holding section 229 that retains the liquid A and provided at a central portion in a direction of the plane and above the measurement chip 60, and thus it is configured to retain various liquids such as a medium, a reagent, and a reaction liquid. This liquid holding section 229 is a space defined by an inner side surface 221a of the casing section 221 and the upper surface 60a of the measurement chip 60.

According to the present embodiment, a liquid introducing section 230 and a liquid discharging section 231 are provided in the vicinity of one end and in the vicinity of the other end, respectively, of an upper part of the liquid holding section 229. The liquid introducing section 230 introduces a predetermined liquid into the liquid holding section 229, and the liquid discharging section 231 discharges the predetermined liquid held in the liquid holding section 229. The liquid introducing section 230 and the liquid discharging section 231 are configured to be able to perform discharging and introducing operations at the same time. For example, in a case where a medium G is held in the liquid holding section 229, a reaction liquid H is introduced into the liquid holding section 229 by the liquid introducing section 230 while discharging the medium G to the outside by the liquid discharging section 231. Thereby, the medium G which has been held in the liquid holding section 229 is replaced with the reaction liquid H. Also, with the present method, by causing the reaction of the microparticle M and measuring fluorescence from the microparticle M, it is found that an intensity stronger than that of the microparticle which does not react is obtained (FIG. 12D).

Figure 12B:
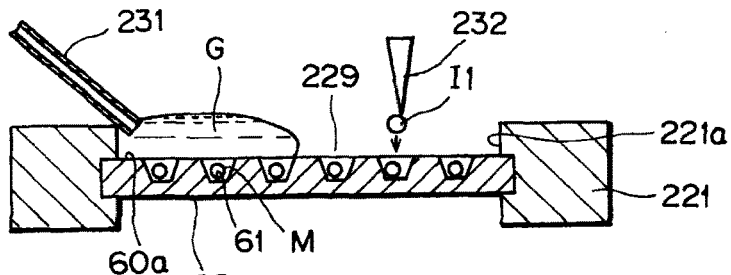
Figure 12C:
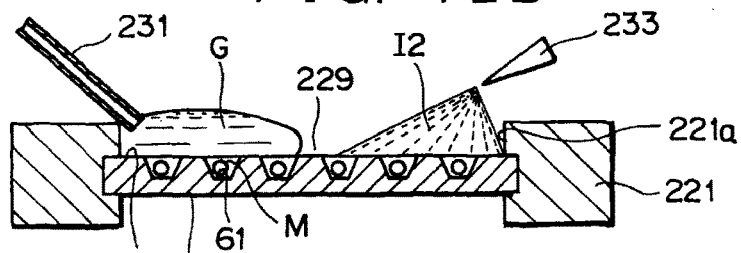
Figure 12D:
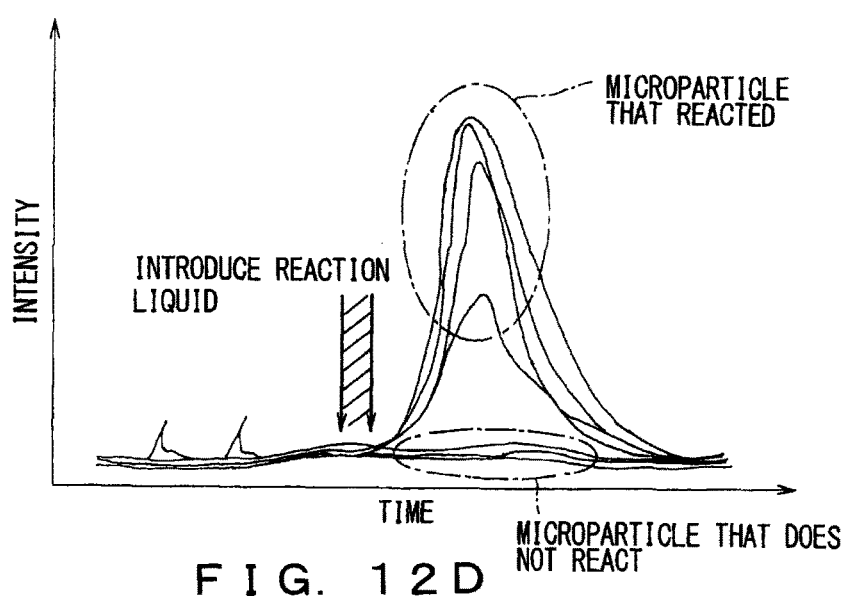
FIG. 12D is a graph showing a temporal change of a detected intensity.

Instead of the liquid introducing section 230, a dropping section 232 may be provided which drops a liquid such as a reagent as a drop I1 for each well in a state where a predetermined amount of medium G has been discharged outside until a liquid surface level of the medium G comes to or to the vicinity of an upper surface of the measurement chip (FIG. 12B), or a spraying section 233 may be provided which sprays a liquid such as a reagent as mist I2 to a predetermined region including a plurality of wells in a state where a predetermined amount of discharged medium G is discharged outside until a liquid surface level of the medium G comes to an upper surface of the measurement chip (FIG. 12C). When the spraying section 233 is placed as shown in FIG. 12C, a mist amount of the mist I2 is greater for a well nearer the casing section 221, and a mist amount of the mist I2 becomes less as it becomes farther from the casing section 221. Thus, a concentration of mist I2 introduced into each well can be made to vary by changing a position at which the spraying section 233 is attached with respect to the measurement chip 60.

In the embodiment shown in FIG. 12A, by making use of the fact that, after introduction of a reaction liquid, temporal variation of a fluorescence intensity of a microparticle in each well of the measurement chip is measured as shown in FIG. 12D, the image analyzing section 15 may continuously measure the temporal variation and, based on the result of a measurement, identify the well for which a sample is to be collected. For example, with temporal variation data of the fluorescence intensity, a difference value between its peak value and a base value to be described later is compared with an arbitrary threshold, and a sample having a peak value exceeding the threshold can be determined as a collecting target, or alternatively, the sample having a peak exceeding the threshold can be excluded from a collecting target. Thereby, collecting can be performed by selecting whether or not there is a reaction of the microparticle.

Here, the base value is defined by, for example, (i) a minimum value during the measurement, (ii) an average until a specified measurement time (i.e., an average value of values before introduction of a liquid), (iii) an average of values when a certain reaction liquid is introduced (e.g., an average value of value when a liquid which should not react is flowed), and (iv) zero (in this case, only the peak is used). Regarding the peak, in order to distinguish from a noise, a moving average can be taken, and in order to determine a significant difference, based on a standard deviation σ, a difference that is less than or equal to a specified criterion may be excluded.

Here, a critical position where the medium G can be discharged by the liquid discharging section 231 is the upper surface 60a of the measurement chip 60, and, in practice, the medium G slightly remains. Even in this state, as shown in FIG. 13A, by dropping a liquid such as a reagent as a liquid drop I1 towards the center of the well 61 containing a microparticle M (cell) therein, since the vicinity of the microparticle M is substantially filled with an intended reagent, the microparticle can be reacted.

In a case where it is desired to avoid mixing with an adjacent well, as shown in FIG. 13B, by drying the measurement chip 60 after discharging the liquid and making a surface level of the liquid contained in the well 61 into a state where it is lower than the upper surface 60a of the measurement chip 60, reaction can be performed while completely isolating the wells.

In FIGS. 12B and 12C, the screening apparatus 1 is provided with the dropping section 232 and the spraying section 233. However, it is not limited thereto, and a dropping process and a spraying process may be performed outside the apparatus without providing a dropping section and a spraying section in the screening apparatus 1.

As a variant of the liquid holding section 229, partitioning sections 235 which divides a planar region of the liquid holding section 229 into five regions 234a to 234e may be provided as shown in FIG. 14. When divided into a plurality of regions in this manner, a liquid of any kind can be introduced into each region and cause the microparticle to react. When the partitioning section 235 is used, a liquid introducing section/liquid discharging section may be provided in each region, or may be provided in a part of a plurality of regions.

Also, the present embodiment employs a method in which, firstly, a single microparticle M is placed in the well 61, and then a liquid is introduced into the well to cause reaction of a microparticle M. To the contrary to this method, it is also possible to firstly cause the microparticle M to react and thereafter place a single microparticle M in the well 61.

Specifically, as shown in FIG. 15A, firstly, a liquid containing a large amount of cells m as the microparticles M is placed into a container 240, and thereafter, a high-concentration liquid K1 containing a substance to be reacted k such as an antibody, a chemical compound or the like is placed into the container 240, and, reaction is waited for a predetermined time. At this time, some of the cells m reacts with the substance to be reacted k and become reacted cells m1 (in FIG. 15A, two cells react). Then, in order to reduce the concentration of the substance to be reacted k, a liquid K2 such as a specific amount of medium is placed into the container 240, and reaction is waited again for a predetermined time. Then, a predetermined cell m which did not react with the first high concentration reacts and becomes a reacted cell m1 (in FIG. 15A, one cell newly reacts). Thereafter, an operation of adding the liquid K2 is repeated to gradually reduce the concentration the substance to be reacted k, and the predetermined cell m is reacted at each concentration (in FIG. 15A, six cells m finally reacts).

Thereafter, a liquid in the container 240 is introduced into the liquid holding section 229 and each cell is received in the well 61. Then, the reacted cell m1 is sucked and collected cell-by-cell with the capillary 140 of the suction-ejection capillary 140, and the collected reacted cell m1 is cultured and analyzed. According to this method, suction and collecting on a cell-by-cell basis can be achieved and also detection accuracy can be improved irrespective of the reaction characteristic of the cell.

Also, contrary to the above methods, the concentration of the substance to be reacted k in the container 240 may be gradually increased. Further, the reagent used in the reaction is not limited to only one kind, and may be a plurality of reagents. The cell to be reacted is not limited to only one kind, and may be a plurality of kinds.

A variant of the measuring section 14A will now be described.

As has been described above, the measuring section 14 acquires the position information of the microparticle by a transmitted light, a reflected light or the fluorescence on a cell-by-cell basis. However, there may be a rare case in which a plurality of microparticles is retained in a single well. Also, even if a single microparticle is retained in a single well, since there is a variation in the size of the microparticles, when the target sample is a microparticle having a smaller size than that of the well, it is unclear as to which position in the depth direction of the well the microparticle is placed and thus measurement cannot be performed accurately.

Accordingly, as shown in FIG. 16, the measuring section 14 detects a surface position of the measurement chip 60 based on optical information about the measurement chip which is obtained by illuminating the measurement chip 60. Based on a particle size of the microparticle M which is a target sample and a dimension of the well, the measuring section 14 corrects a focus position of the light illuminated on the microparticle M in a depth direction (a thickness direction of the measurement chip 60) by a predetermined amount (3D measurement). Specifically, the image analyzing section 15 calculates the center position of the microparticle based on the surface position of the measurement chip 60 and the size of the microparticle M. In accordance with the aforementioned center position, the measuring section 14 illuminates at a substantially central position of the microparticle M retained in the well 61. For example, in a case where the microparticle M has an outer diameter of approximately 20 μm and the well has an outer diameter of 30 μm and a depth of approximately 25 μm, the upper surface 60a of the measurement chip 60 is taken as a reference surface position (±0) and the focal point of the light illuminated is changed to a position of −10 μm, which is approximately a radius of the microparticle, from the reference surface position.

In this manner, when the depth of the well is approximately 50% to 100% of the outer diameter of the well, and more preferably 70% to 80% of the well, a single microparticle can be appropriately retained and collected in a single well. Also, it is preferable that the outer diameter of the microparticle is approximately 50% to 80% of the outer diameter of the well.

With the aforementioned focal point changing control, with the transmitted light, it is possible to analyze and identify a number of microparticles M in the well 61, and collecting accuracy on a particle-by-particle basis can be improved. With the fluorescence, since the highest fluorescence luminance among the microparticles M can be measured, it is possible to improve an analysis result.

Particularly, since the microparticle M is often placed at the bottom part of in the well 61, a sufficient fluorescence luminance may not be obtained and an accurate measurement may not be performed in a state where the focus is at the surface of the measurement chip (0 μm). According to the present disclosure, a center position of the microparticle is calculated based on a shape of the well 61 and the dimension of the microparticle M, and a measurement result of a high accuracy can be obtained by focusing on a calculated position. For example, when a dimensional relationship between the well 61 and the microparticle M is as shown in FIG. 16, a measurement result of a highest accuracy can be obtained by focusing on a position at −10 μm shown in FIG. 16.

Further, it is preferable to obtain information by changing a focus position between +10 μm and −20 μm to cover from the bottom part of the well to a surface part of the measurement chip at an interval of the same extent as the radius of the microparticle, for example, at a 10 μm interval in FIG. 16. For example, in the right most well in FIG. 16, in a case where strong fluorescence information was obtained at both a −10 μm position shown in (b) and a +10 μm position shown in (d), it is determined that two microparticles exist. According to this method, the number of microparticles existing in one well can be counted.

Also, in the present embodiment, it is preferable to rinse the distal end portion 142b of the capillary 142 before suction of the microparticle M, since, as has been described above, various liquids and microparticles M may attach to the distal end portion 142b of the capillary 142 during the suction and ejection of the microparticle M. In such a rinsing, the well 51 in the receiving plate 50 may be used as a rinsing reservoir, or a rinsing reservoir provided separate from the well may be used.

For example, as shown in FIG. 17A, when a suction-ejection operation is performed, there may be a case where a microparticle M attaches to an inner wall 251 and/or an outer wall 253 of the distal end portion 142b. Accordingly, by inserting the distal end portion 142b of the capillary 142 into a rinsing liquid Y contained in the rinsing reservoir X (FIG. 17B), the microparticle attached to an outer wall 253 of the capillary 142 can be removed. Also, by sucking and ejecting the rinsing liquid (FIG. 17C), the microparticle attached to the inner wall 251 of the capillary 142 can be removed.

Further, as shown in FIGS. 18A and 18B, a liquid depth in the suction operation is defined as δ1 (corresponds to depth d2 in FIG. 10D), and a depth of a part of the capillary 142 that is submerged under a liquid surface in the receiving plate 50 during the ejection operation is defined as δ2. Here, it is preferable that a depth δw2 of a part of the capillary 142 that is submerged under a liquid surface in the rinsing reservoir is set so as to be greater than the depth δ2 in the ejection operation (δw2>δ2). By setting in this manner, the outer wall 253 of the capillary 142 is sufficiently rinsed. Further, even in a case where a microparticle M is remaining on the outer wall 253 after the rinsing, since the microparticle is remaining at an upper part of the outer wall 253 of the capillary 142, it is possible to prevent a microparticle which is not a target from falling onto the receiving plate 50 during the ejection operation to the receiving plate 50.

Also, it is preferable that a sucked amount δw1 of the rinsing liquid is set so as to be greater than the depth of liquid δ1 during the suction operation (δw1>δ1). By setting in this manner, in a case where the microparticle M is not ejected and remaining on the inner wall 251 of the capillary 142, there is a greater possibility that it is ejected by sucking a sufficient rinsing liquid. Also, even in a case where a microparticle M is remaining on the inner wall 251 after the present rinsing, since the microparticle is remaining at an upper part of the inner wall 251 of the capillary 142, the remaining microparticle does not have an adverse effect in a subsequent suction operation.

Figure 19A:
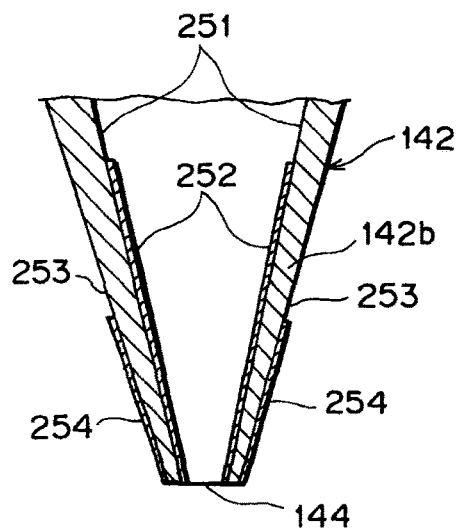
FIG. 19A to 19C are diagrams showing variants of the distal end portion of the capillary.
Figure 19B:
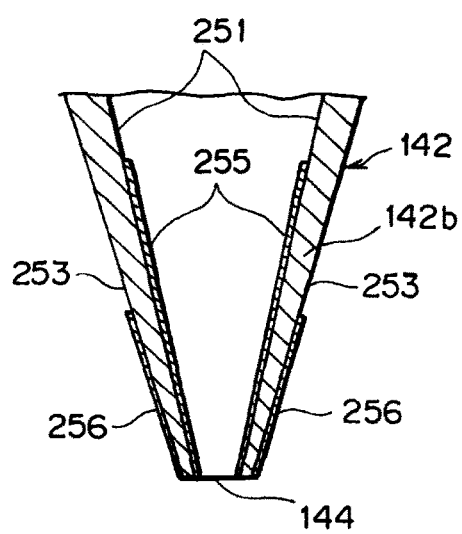
Figure 19C:
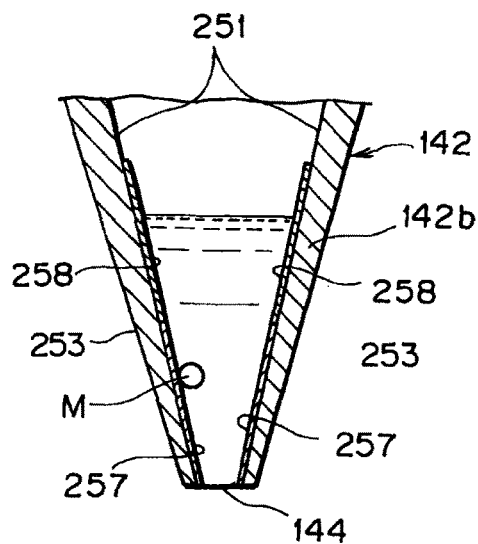

FIGS. 19A to 19C are diagrams showing variations of the distal end portion 142b of the capillary 142.

As shown in FIG. 19A, it is preferable that the inner wall 251 of the distal end portion 142 is provided with a hydrophobic layer 252 (hydrophobized surface) and the outer wall 253 is provided with a hydrophobic layer 254. These hydrophobic layers 252 and 254 are formed by, for example, coating a silicone-based material. By forming the present hydrophobic layers, since various liquids are less likely to remain at the distal end portion 142b during the collecting of the microparticle M, various liquids can be prevented from being transferred to the receiving plate 50.

Alternatively, the inner wall 251 and the outer wall 253 of the distal end portion 142b may be provided with hydrophilic films 255, 256, respectively (see FIG. 19B). The hydrophilic films 255 and 256 are formed with a hydrophilic coating by plasma treatment, for example. With the present hydrophilic film, since a microparticle M such as a cell is less likely to attach to the inner wall 251 and/or to the outer wall 253, an ejection accuracy of microparticle M can be improved.

Alternatively, a distal end side of the inner wall 251 of the distal end portion 142b may be provided with a hydrophilic film 257 and a hydrophobic layer 258 may be provided at an upper part of the hydrophilic process film 257. According to the present configuration, since the distal end side of an inner portion of the capillary 142 is subjected to a hydrophilic treatment and a portion nearer to the proximal end is subjected to a hydrophobic treatment, the microparticle M is less likely to move further towards the proximal end of the capillary 142 during the suction and the microparticle M is less likely to remain in the capillary. Thus, the suction-ejection accuracy can be improved.

A variant of the collecting section 13 will described with reference to FIGS. 20 and 21. The collecting section of the present variant is a mechanism for improving a collecting accuracy in a subsequent suction operation by releasing a residual pressure in the capillary 142 in a current suction operation. Since the configuration of the present variant is the basically same as the collecting section 13, different parts will be described below.

Figure 20:
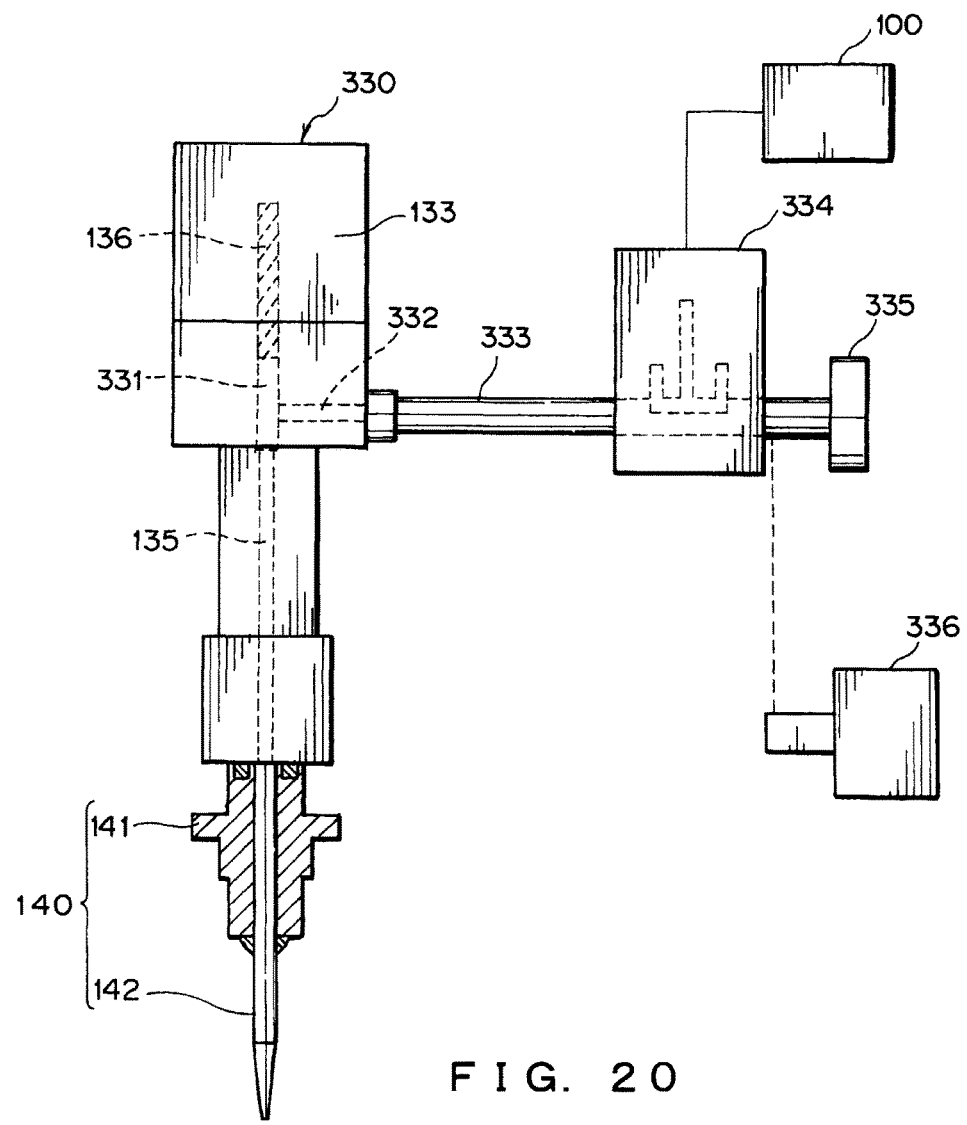
FIG. 20 is a diagram showing a variation of an operating section of FIG. 6.
Figure 21:
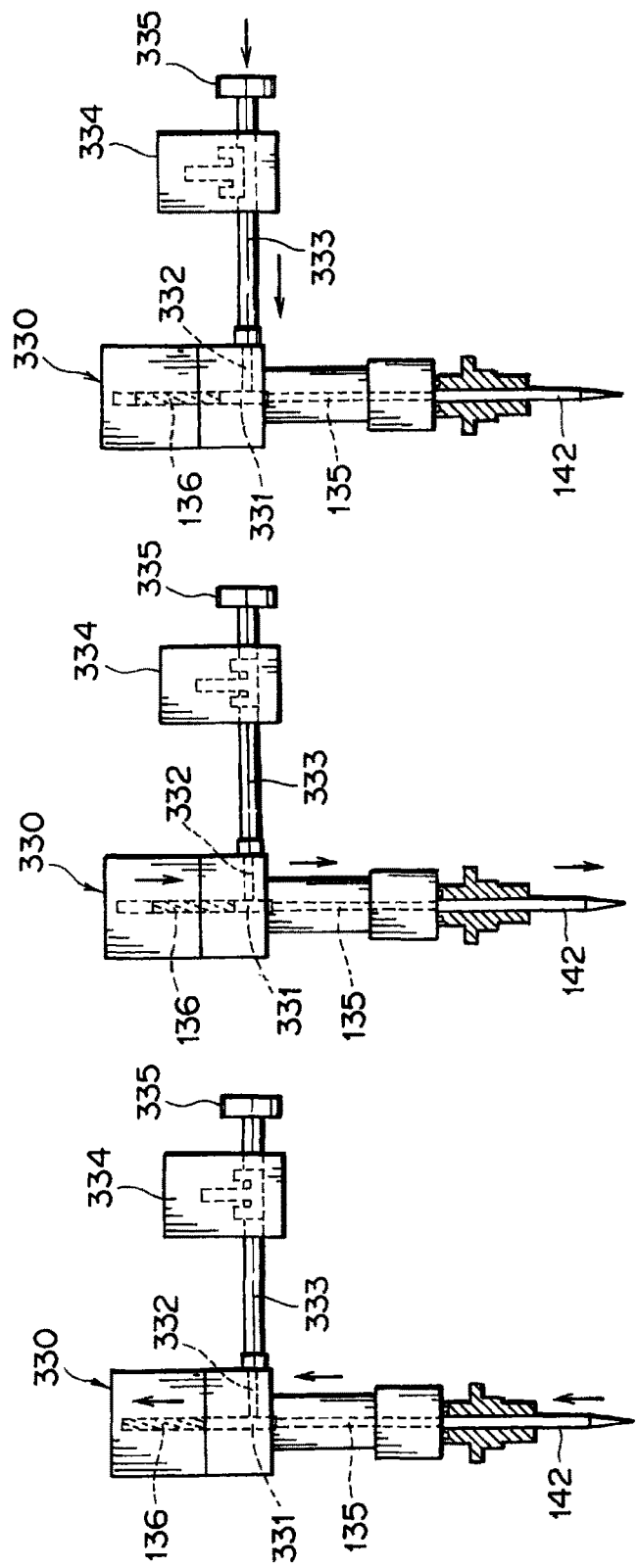
FIGS. 21A to 21C are diagrams showing an operation of the operating section of FIGS. 19A to 19C.

As illustrated in FIG. 20, a collecting section 330 includes a branch path 332 provided at a cylinder 331 of the actuator main body 133, a conduit 333 connected to the branch path 332 and made of an elastic material such as a rubber tube, a solenoid valve 334 (valve section) connected to the conduit, and a dust filter 335 disposed at an opening side of the solenoid valve 334. An inner diameter of the conduit 333 is greater than an inner diameter of the end surface 144 of the capillary 142, and an inner diameter of a channel in the solenoid valve 334 is greater than the inner diameter of the end surface 144 of the capillary 142.

An operation of this collecting section 330 will be described with reference to FIG. 21A. Firstly, with an upward movement of the plunger 136, a liquid containing a microparticle M which is a target sample is sucked by the capillary 142. At this time, since the solenoid valve 334 is closed, an air flow in the branch path 332 does not occur.

Then, the plunger 136 moves downwardly and discharges the liquid containing the target sample M from the capillary 142 (FIG. 21B). At this time, the plunger 136 operates with a displacement greater than a displacement moved through during the suction operation. By this operation, the microparticle M or an entirety of the liquid in the capillary 142 is ejected. Also during this ejection operation, since the solenoid valve 334 is closed, an air flow in the branch path 332 does not occur.

Then, when returning the plunger 136 to a position prior to the suction operation, the solenoid valve 334 is firstly opened, and the plunger 136 is moved upward with the solenoid valve 334 being open (FIG. 21C). At this time, since the dust filter 335 has an open end, and the inner diameter of the conduit 333 and the inner diameter of the flow path in the solenoid valve 334 are greater than the inner diameter at the end surface 144 of the capillary 142, an air flow that is flowing inwardly is produced in the branch path 332 and thus a residual pressure in the capillary 142 is released.

Therefore, according to the present variant, since the microparticle M or an entirely of the liquid in the capillary 142 is ejected during the ejection operation and the residual pressure in the capillary 142 is released in the subsequent suction operation, a collecting accuracy can be further improved.

Note that, in the present variant, although the residual pressure release is performed with a natural aspiration, the solenoid valve 334 may be provided with a pump 336 and air may be forcedly blown into the branch path 332 when returning the plunger 136 to the position prior to the suction operation (FIG. 20). Thereby, the collecting accuracy can be further improved.

Figure 22:
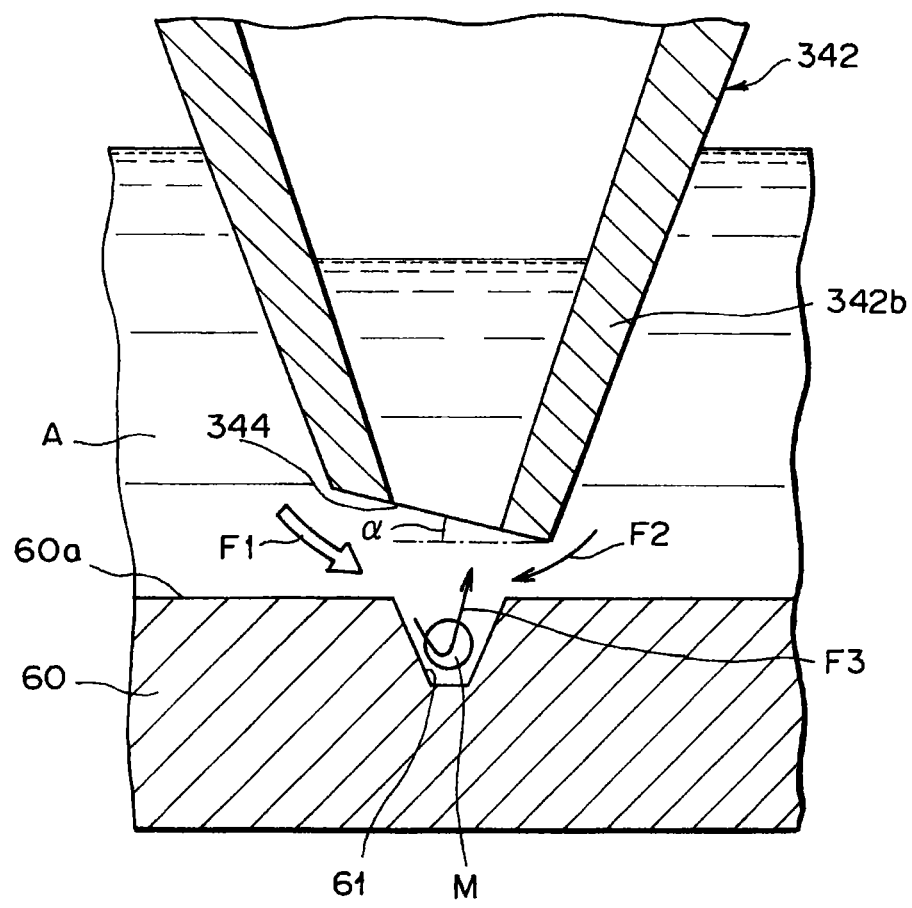
FIG. 22 is a diagram showing a variant of the distal end portion of the capillary.
Figure 23:
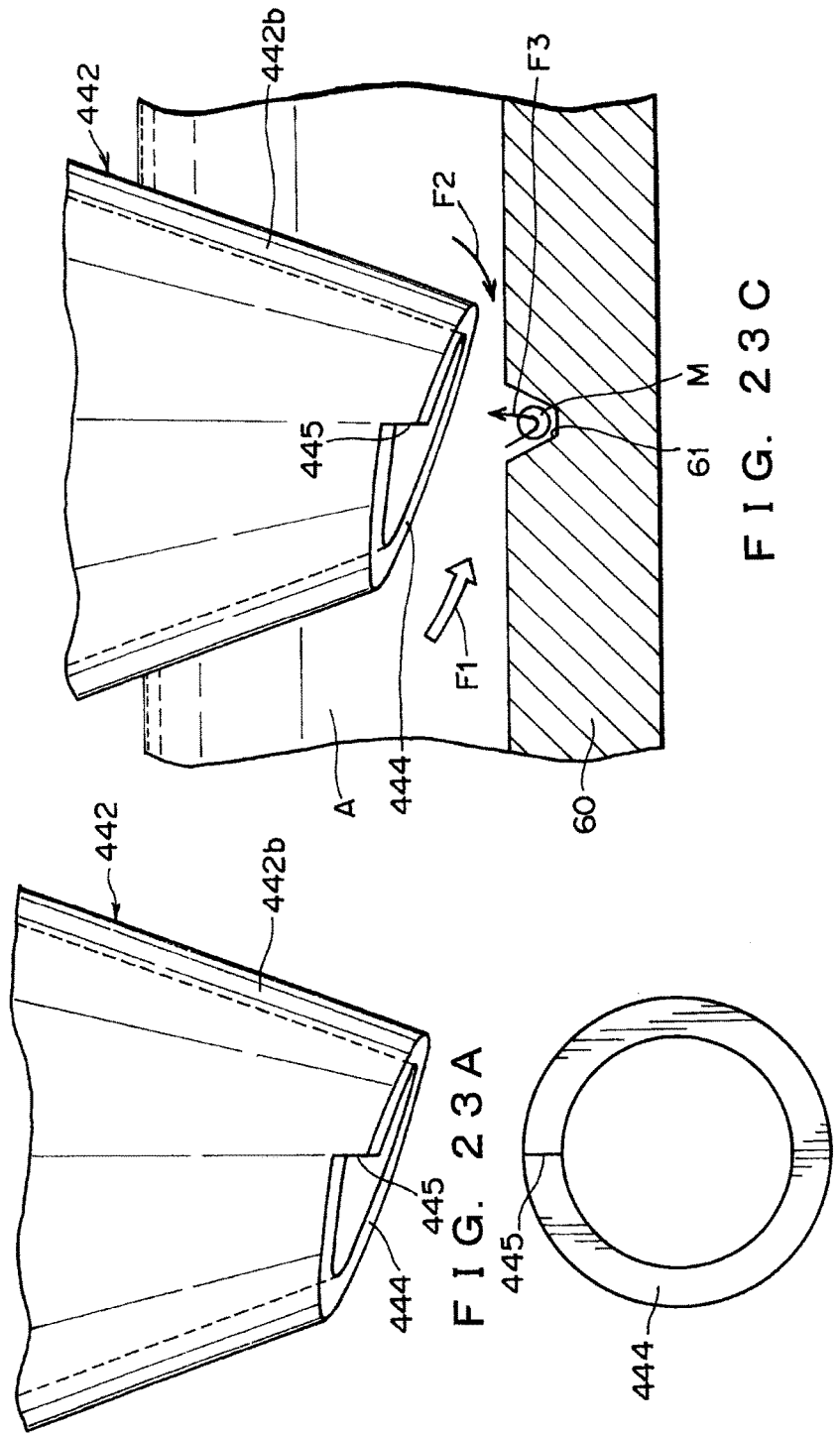

FIGS. 22 and 23 are diagrams showing a variant of the distal end shape of the capillary 142.

As has been described with reference to FIG. 8, since it is sufficient if the liquid flows F1 and F2 having different flow rates on one side and the other side of the capillary 142, respectively, are produced, the shape of the distal end portion 142b of the capillary 142 can be configured as follows. For example, in the variant of FIG. 22, a distal end portion 342b of the capillary 342 has an end surface 344 that forms a predetermined angle α (0°<α<90°) with respect to a horizontal direction. In other words, since the end surface 344 is not parallel to the upper surface 60a of the measurement chip 60, and it is an inclined surface that is inclined with respect to the upper surface 60a, liquid flows F1 and F2 having different flow rates with respect to each other can be produced and an upward one way flow F3 can be produced in the well 61.

Further, in variants shown in FIGS. 23A to 23C, a distal end section 442b of a capillary 442 has a helical end surface 444 and a stepped portion 445. The end surface 444 is an inclined surface that is inclined with respect to the upper surface 60a of the measurement chip 60, and the stepped portion 445 is formed in the inclined surface. With this stepped portion 445, a helical vortex is produced in the vicinity of the end surface 444, and liquid flows F1 and F2 having flow rates largely differing from each other can be produced. Thus, the upward one way flow F3e can be positively produced in the well 61, and an accurate suction of the microparticle M can be achieved.

Figure 24:
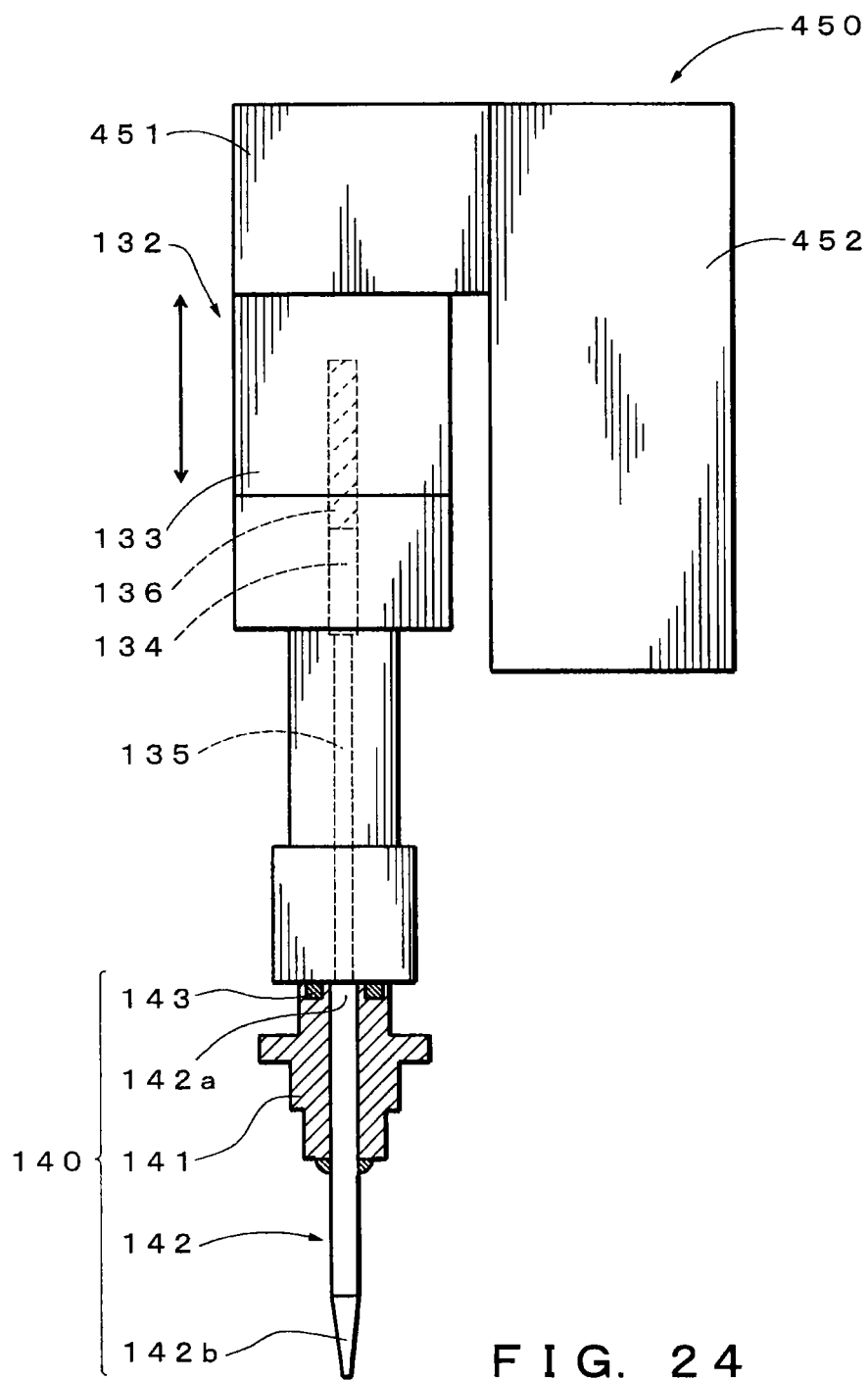
FIG. 24 is a side view showing a variant of the collecting section of FIG. 1.
Figure 25:
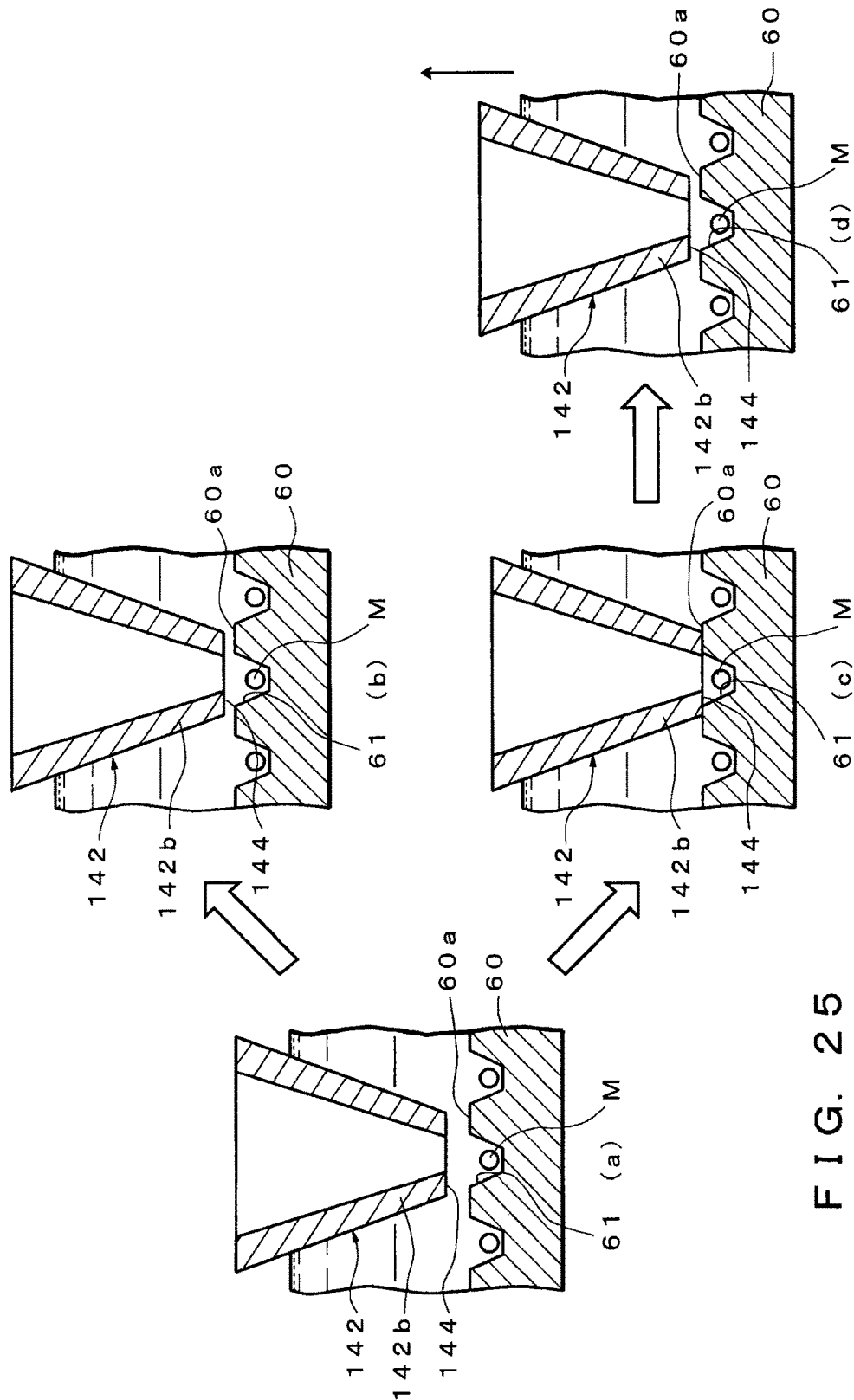
FIG. 25 is a diagram for explaining, in parts (a) to (d), an operation of the collecting section of FIG. 24.
Figure 26A:
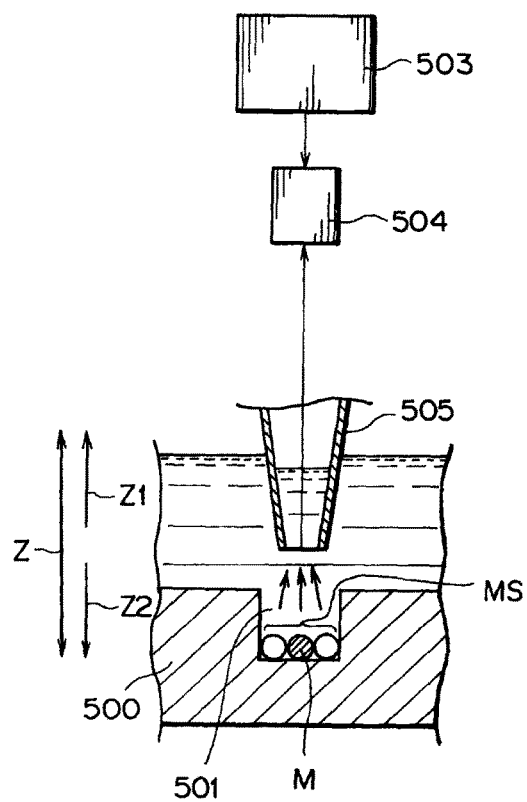
FIGS. 26A and 26B are diagrams showing an operation of a screening apparatus of the related art.
Figure 26B:
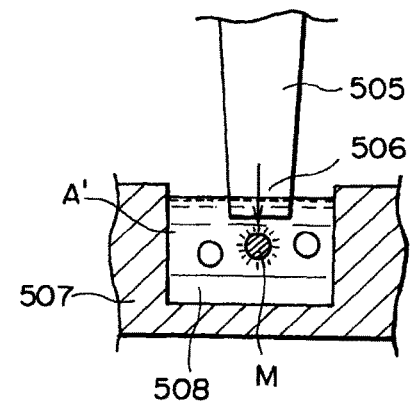

FIG. 24 is a perspective view showing a variant of the collecting section 13 of FIG. 7, and FIG. 25 is a diagram for explaining, in parts (a) to (d), an operation of the collecting section of FIG. 24. The collecting section in this variant has a detecting section and a vertical movement stage to be described below in addition to the configuration of the collecting section 130 of FIG. 7. Note that the same numerals are used for the same configuration as the collecting section 130 and explanation thereof is omitted.

As shown in FIG. 24, a collecting section 450 includes a detecting section 451 (detecting mechanism) that is disposed above the actuator 132 and detects a load on the suction-ejection capillary 140 and a vertical movement stage 452 (moving mechanism) that moves the suction-ejection capillary 140 in a vertical direction. The detecting section 451 is, for example, a pressure sensor, and detects a pressure on the measurement chip 60 from the suction-ejection capillary 140. The control unit 100 determines whether or not the distal end portion 142b of the capillary 142 and the upper surface 60a of and the measurement chip 60 are in contact, and transmits a signal corresponding to a determination result to the vertical movement stage 452. The vertical movement stage 452 moves the suction-ejection capillary 140 in a vertical direction in response to the signal from the control unit 100 by driving a motor, not shown.

The collecting section 450 of the present variant operates as follows. As shown in FIG. 25, in parts (a) to (d), the control unit 100 receives a signal from the detecting section 451 and determines whether or not the end surface 144 of the suction-ejection the capillary 142 is in contact with the upper surface 60a of the measurement chip 60. In a case where pressure detected by the detecting section 451 is zero, the control unit 100 determines that the end surface 144 is not in contact with the upper surface 60a, and the suction operation of the microparticle M is performed (part (b) in FIG. 25). On the other hand, in a case where the pressure detected by the detecting section 451 is greater than zero, the control unit 100 determines that the end surface 144 of the suction-ejection capillary 142 and the upper surface 60a of the measurement chip 60 are in contact (part (c) in FIG. 25) and moves the vertical movement stage 452 upwardly move the suction-ejection capillary 140 by a predetermined distance (part (d) in FIG. 25). Thereafter, the suction operation of the microparticle M is performed at a position after the adjustment.

Here, in order to suck only the microparticle which is a target sample, it is necessary to positively suck a microparticle M which is directly under the suction-ejection capillary and not to suck neighboring microparticles. As has been described above, ideally, the smaller the distance L between the end surface 144 of the suction-ejection capillary 140 and the upper surface 60a of the measurement chip 60, the more accurately the sucking of only a target microparticle M can be performed. On the other hand, due to a relative movement error, a warping of the measurement chip 60 or an analysis error, there may be a case where an intended distance L between the end surface 144 of the suction-ejection the capillary 142 and the upper surface 60a of the measurement chip 60 is not achieved. In such a case, when the distance L becomes zero, the suction-ejection capillary 142 may come into contact with the measurement chip 60 and it may not be possible to perform suction due to a vacuum state.

According to the present variant, in a case where the suction-ejection capillary 142 and the measurement chip 60 are in contact, since they are spaced apart, it is possible to positively prevent a state in which the microparticle M cannot be sucked by the suction-ejection capillary 142. Since the state in which suction is not possible can be positively avoided, the distance L between the end surface 144 of the suction-ejection capillary 142 and the upper surface 60a of the measurement chip 60 can be made as small as possible, and it is possible to positively suck only the microparticle M which is a target sample.

In the present embodiment, although the distal end portion 142b of the capillary 142 has a substantially cylindrical shape, it may also have a substantially square tubular shape. Although the well 61 has a horizontal sectional shape which is generally circular, it may also be generally rectangular. Also, a horizontal sectional shape of the distal end portion of the capillary may be nonsimilar or have a different shape from the horizontal sectional shape of the well. For example, a horizontal sectional shape of the distal end of the capillary is generally circular, and a horizontal sectional shape of the well may be generally rectangular. With such a configuration, effects similar to the aforementioned effects can be achieved.

In the above, the present disclosure obtained by the present inventors has been described specifically based on the embodiments. However, the present disclosure is not limited to the embodiments described above, and it can be modified without departing from the spirit and scope of the present disclosure.

What is claimed is:

1. A screening apparatus that searches for a predetermined microparticle based on optical information emitted from microparticles to selectively pick up the microparticle searched for, the screening apparatus comprising:
a measurement chip that is made of a light permeable material, the measurement chip having an upper surface with multiple wells formed therein, each of the wells retaining a liquid including a microparticle and having a size corresponding to a single microparticle;
a measuring section that includes a light source and acquires optical information associated with the microparticles, the optical information being obtained by illuminating the microparticles retained in the measurement chip with the light source;
an analyzing section that analyzes the optical information to extract optical information associated with the microparticles retained in the wells;
a suction-ejection capillary that has a central axis of a distal end of the suction-ejection capillary displaced from a central axis of each of the wells and the distal end being positioned outside of each of the wells while the suction-ejection capillary is sucking each microparticle, wherein the central axis of the distal end and the central axis of each well are parallel and along with a longitudinal direction of the distal end;
a receiving plate that receives a microparticle selectively picked up by the suction-ejection capillary from a well of the measurement chip based on a result of the analysis;
a moving section that is capable of moving the measurement chip and the receiving plate with respect to the measuring section;
a collecting section having a pump and the suction-ejection capillary, the collecting section being for collecting the selectively picked microparticle in the well provided in the measurement chip, the microparticle being sucked by the suction-ejection capillary and ejected at a predetermined position on the receiving plate,
an outer dimension of the distal end of the suction-ejection capillary being greater than a width of each well, at its largest width, formed in the measurement chip,
the suction-ejection capillary sucking the selected microparticle which is a target sample at a position where the distal end of the suction-ejection capillary and the upper surface of the measurement chip are spaced apart by a predetermined distance in the longitudinal direction; and
a controller programmed to control the suction-ejection capillary to suck the selectively picked microparticle at the position where the suction-ejection capillary is spaced apart from the upper surface of the measurement chip by the predetermined distance, and at a position where the central axis of the well and the central axis of the suction-ejection capillary are displaced.

2. The screening apparatus according to claim 1, further comprising:
a discharging section that discharges a liquid in a liquid holding section provided on the measurement chip; and
an introducing section that introduces a predetermined liquid onto the liquid holding section,
a liquid on the measurement chip being replaced by discharging the liquid on the liquid holding section by the discharging section and introducing the predetermined liquid by the introducing section.

3. The screening apparatus according to claim 2, wherein, with the liquid in the liquid holding section being discharged by a predetermined amount until reaching an upper surface of the measurement chip or a vicinity thereof, an arbitrary reagent is dropped into each well.

4. The screening apparatus according to claim 2, wherein with the liquid in the liquid holding section being discharged by a predetermined amount until reaching an upper surface of the measurement chip or a vicinity thereof, an arbitrary reagent is sprayed on a predetermined region of the measurement chip.

5. The screening apparatus according to claim 2, wherein at least one partitioning portion is provided on an upper surface of the measurement chip, and
a discharging section and introducing section is provided for each of at least two regions divided by the partitioning portion.

6. The screening apparatus according to claim 1, wherein the selected microparticle is contained in a single container before being held on the measurement chip,
wherein a reactant that reacts with the selected microparticle is added into the container for several times with a concentration of the reactant being gradually changed, and
wherein a liquid in the container that contains the selected microparticle reacted with the reactant is introduced onto the measurement chip.

7. The screening apparatus according to claim 1, wherein the measuring section detects a surface position of the measurement chip based on optical information related to the measurement chip which is obtained by illuminating the measurement chip,
the analyzing section calculates a center position of the selected microparticle from the surface position and a size of the selected microparticle, and
the measuring section illuminates a substantially center position of the selected microparticle retained in the well based on the center position.

8. The screening apparatus according to claim 1, wherein the collecting section rinses the distal end of the suction-election capillary before suction of the selected microparticle.

9. The screening apparatus according to claim 1, wherein a hydrophobic surface is formed at least on an inner surface of the distal end of the suction-ejection capillary.

10. The screening apparatus according to claim 1, wherein the pump includes a tubular pump body and a plunger that is movable in a vertical direction within the pump body, and
wherein the pump body includes a cylinder provided in communication with a conduit of the suction-ejection capillary and through which the plunger is movable, and a branched path provided in the cylinder.

11. The screening apparatus according to claim 10, wherein
   a valve section is connected to the branch path via a conduit,
   an inner diameter of the valve section and the conduit is greater than an inner diameter of the suction-ejection capillary.

12. The screening apparatus according to claim 11, wherein, after sucking the selected microparticle by the suction-ejection capillary, the valve section is opened to release a residual pressure in the suction-ejection capillary.

13. The screening apparatus according to claim 12, wherein a displacement of the plunger at a time of ejecting the selected microparticle is greater than a displacement of the plunger at a time of suction of the selected microparticle.

14. The screening apparatus according to claim 1, wherein the suction-ejection capillary sucks a liquid of a predetermined amount before sucking the selected microparticle, and thereafter sucks the selected microparticle.

15. The screening apparatus according to claim 1, wherein
   the collecting section further includes a detecting mechanism that detects a contact between the distal end of the suction-ejection capillary and the upper surface of the measurement chip, and a moving mechanism that adjusts a distance between the distal end of the suction-ejection capillary and the upper surface of the measurement chip, and
   in a case where the suction-ejection capillary is in contact with the measurement chip, the suction-ejection capillary is moved to the position where the distal end of the suction-ejection capillary and the upper surface of the measurement chip are at the predetermined distance.

16. The screening apparatus according to claim 1, the screening apparatus performing a screening method comprising:
   acquiring position coordinate information of each well in the measurement chip;
   acquiring optical information about each microparticle by illuminating each microparticle in each well;
   identifying the microparticle as the selectively picked microparticle which satisfied at least one predetermined collecting condition as the target sample, based on the acquired position coordinate information and the acquired optical information;
   acquiring a center position of the suction-ejection capillary for sucking and ejecting the target sample;
   setting a position at which the suction-ejection capillary sucks the selected microparticle;
   moving the well to match the set position; and
   sucking the microparticle which is the target sample at the seta position.

17. The screening apparatus according to claim 1, wherein the measuring section acquires temporal variation of a fluorescence intensity of each microparticles as the optical information, and the analyzing section performs determination on each microparticle to be collected based on the optical information.

* * * * *